(12) United States Patent
Saha

(10) Patent No.: US 7,936,458 B2
(45) Date of Patent: May 3, 2011

(54) POLARISCOPE TOY AND ORNAMENT WITH ACCOMPANYING PHOTOELASTIC AND/OR PHOTOPLASTIC DEVICES

(76) Inventor: Pamela Saha, Wellsville, NY (US)

( * ) Notice: Subject to any disclaimer, the term of this patent is extended or adjusted under 35 U.S.C. 154(b) by 0 days.

(21) Appl. No.: 12/288,916

(22) Filed: Oct. 24, 2008

(65) Prior Publication Data

US 2009/0091046 A1    Apr. 9, 2009

Related U.S. Application Data

(62) Division of application No. 11/259,595, filed on Oct. 26, 2005, now Pat. No. 7,477,386.

(60) Provisional application No. 60/621,660, filed on Oct. 26, 2004.

(51) Int. Cl.
  G01B 5/30    (2006.01)
  G01B 7/16    (2006.01)
  G01L 1/00    (2006.01)
  G01N 3/00    (2006.01)
  G01J 4/00    (2006.01)
  A63H 33/00    (2006.01)

(52) U.S. Cl. .......... 356/364; 73/760; 356/365; 356/366; 446/69; 446/491

(58) Field of Classification Search ........... 356/32–35.5, 356/364–370, 616–617; 264/239
See application file for complete search history.

(56) References Cited

U.S. PATENT DOCUMENTS

| | | | | |
|---|---|---|---|---|
| 1,436,028 A * | 11/1922 | Flemming | ........................ | 40/327 |
| 1,883,704 A * | 10/1932 | Goodwin | ....................... | 156/213 |
| 2,874,649 A * | 2/1959 | Pelletier | ........................ | 426/249 |
| 3,034,395 A * | 5/1962 | Zandman | ........................ | 356/34 |
| 3,071,502 A * | 1/1963 | Zandman | ........................ | 156/196 |
| 3,122,684 A * | 2/1964 | Genin | ............................ | 335/285 |
| 3,157,912 A * | 11/1964 | Lisczawka | ........................ | 425/2 |
| 3,373,652 A * | 3/1968 | Flader | .............................. | 356/33 |
| 3,555,475 A * | 1/1971 | Szczepanski | ................. | 355/306 |
| 3,607,584 A * | 9/1971 | Becht | ............................. | 359/883 |
| 4,008,960 A * | 2/1977 | Reytblatt | ........................ | 356/33 |
| 4,109,515 A * | 8/1978 | Swenson, Jr. | ................... | 73/800 |
| 4,306,373 A * | 12/1981 | Chatani et al. | ................ | 446/121 |

(Continued)

OTHER PUBLICATIONS

Precision Casting of Epoxy-Resin Photoelastic Models, H. Fessler & M. Perla, The Journal of Strain Analysis for Engineering Design, vol. 8, No. 1 / 1973, pp. 30-34.*

Rossing & Chiaverina, Light Science: Physics and the Visual Arts, ISBN 0-387-98827-0, 1999 Springer-Verlag New York, Inc., pp. 102, 171.*

(Continued)

*Primary Examiner* — Gregory J Toatley
*Assistant Examiner* — Jarreas C Underwood
(74) *Attorney, Agent, or Firm* — Hyra IP, PLC; Clifford D. Hyra

(57) ABSTRACT

A variety of toy polariscopes are simpler in design and less costly than precision instruments used in scientific research and stress analysis of materials and structures. The toy polariscopes are designed for a variety of objects that may exhibit photoelastic properties such as glass, plastic, Plexiglas, gel candle material and other gels, and even edible photoelastic objects. They are specially designed for objects of various sizes with a variety of purposes such as objects to enhance learning in a variety of conditions and experiences. Special objects are designed to go with the toy polariscopes such as edible and inedible photoelastic objects, photoelastic candle material, a variety of photoelastic/photoplastic stands capable of a variety of displays in interaction with other designed photoelastic objects capable of a variety of interaction and displays. Other optical phenomena may also be observed.

14 Claims, 18 Drawing Sheets

U.S. PATENT DOCUMENTS

| | | | |
|---|---|---|---|
| 4,668,085 A * | 5/1987 | Pitt et al. | 356/32 |
| 4,948,255 A * | 8/1990 | Watanabe | 356/367 |
| 5,093,049 A * | 3/1992 | Uehara et al. | 264/2.2 |
| 5,968,302 A * | 10/1999 | Gifford | 156/245 |
| 6,022,279 A * | 2/2000 | Yamagishi et al. | 473/353 |
| 6,713,007 B2 * | 3/2004 | Iwami | 264/254 |
| 6,985,214 B2 * | 1/2006 | Szaroletta et al. | 356/34 |
| 7,430,038 B2 * | 9/2008 | Szaroletta et al. | 356/32 |

OTHER PUBLICATIONS

Fessler & Perla, Precision Casting of Epoxy-Resin Photoelastic Models, The Journal of Strain Analysis for Engineering Design, vol. 8, No. 1 / 1973, pp. 30-34.*

Richards & Mark, Gelatin Models for Photoelastic Analysis of Gravity Structures, Experimental Mechanics, vol. 6, No. 1 / Jan. 1966, pp. 30-38.*

* cited by examiner

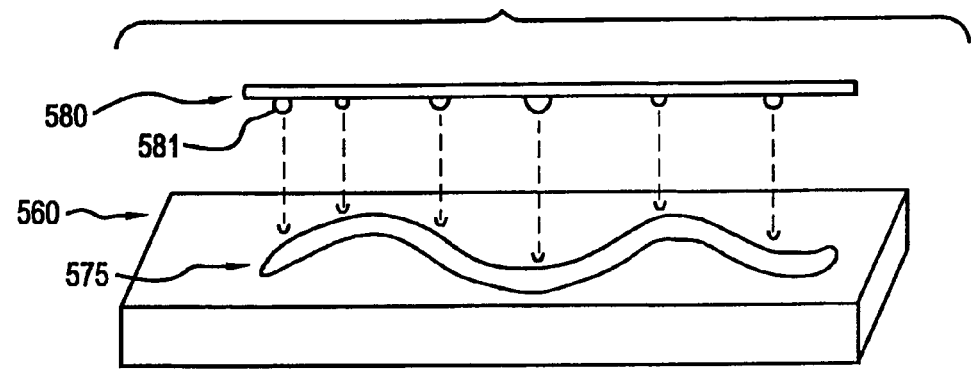
FIG. 12
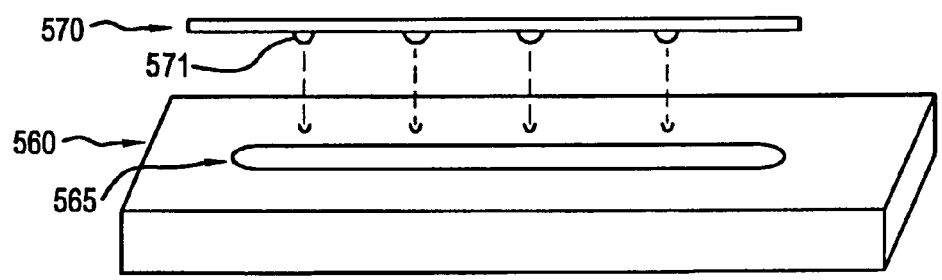
FIG. 13
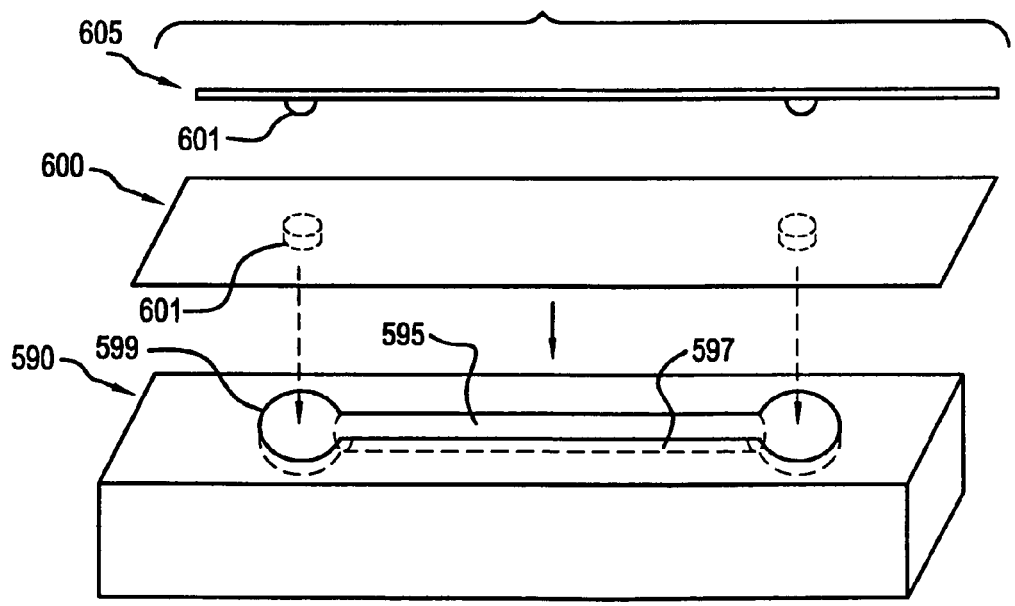

POLARISCOPE TOY AND ORNAMENT WITH ACCOMPANYING PHOTOELASTIC AND/OR PHOTOPLASTIC DEVICES

This application is a divisional application of U.S. application Ser. No. 11/259,595, filed Oct. 26, 2005 now U.S. Pat. No. 7,477,386.

This application claims the benefit of U.S. Provisional Application No. 60/621,660, filed Oct. 26, 2004, which is hereby incorporated by reference in its entirety.

BACKGROUND OF THE INVENTION

Polariscopes are used for scientific research, particularly, for the study of stress analysis of materials and structures. Such polariscopes are precision instruments and cost thousands of dollars.

Needs exist for simpler, less costly polariscopes, as well as polarizing devices, designed specifically for amusement in a variety of contexts to entertain and to stimulate an interest in science and engineering in children and adults.

SUMMARY OF THE INVENTION

The present invention includes a variety of toy polariscopes some of which are simpler in design and less costly than the precision instruments used in scientific research and stress analysis of materials and structures. While the invention is not restricted to low cost forms, all of the polariscope toys of the present invention are designed for purposes other than precision scientific measurements related to stress analysis. The devices are designed to amuse, add aesthetics, provide ornamentation, or add features on sports equipment. The devices of the present invention may also serve as a visual reward for completing tasks in learning games when working with both humans and animals. These toys allow children and adults to explore and observe photoplastic and photoelastic stress patterns in various objects. Objects that may exhibit these properties are glass, plastic, Plexiglas, and even edible photoelastic objects. Other optical phenomena may also be observed, such as optical phenomena in the sky, in bodies of water, or other environmental settings.

An embodiment of the present invention is composed of two polarizing films that are free to rotate with respect to one another to control transmission of light. The polarizing films are also located at an adjustable distance from one another. For larger sized toy polariscopes, the space between the films allows for placement of larger objects or multiple objects between the films. Additionally, a user's hands or arms and\or instruments for manipulation may fit between the films.

A stand may also be provided for holding an object or objects. The stand displays the photoelastic objects. Photoelastic objects may include building blocks, parts of construction kits, the display stand itself; objects that move mechanically, vibrate, rotate, are suspended or levitated by magnetic fields, or moving by other devices such as heat, light, solar energy, or electricity. The stand is placed between the polarizing films or other combinations of optical films, devices and mirrors. The stand itself may be cast to create fixed photoplastic stress patterns. Detachable or permanently attached hooks, platforms, frames and other devices enhance the viewing experience. The display stand/stands can come in a number of variable forms and can be assembled in a variety of patterns such that like the flexible photoelastic objects the stands/parts of stands are themselves another set of construction and display objects with photoplastic effects.

Specially designed photoelastic objects act as building kits. The edible or non-edible photoelastic objects can be assembled and disassembled in a variety of construction patterns. Furthermore, stands may also be assembled and disassembled in a variety of configurations.

The photoelastic objects show photoelastic fringes with or without the aid of a toy polariscope. The fringes may-be enhanced when assembled. The objects may be cast such that the objects have permanent photoplastic fringes as well as fringes created by deformation. The objects may utilize magnets or other systems for assembly. The magnets may be completely embedded within the plastic, glass or Plexiglas. This produces an impression of the magnetic objects floating within the substrate. Alternatively, a ferromagnetic material may be incorporated into the photoelastic objects. The ferromagnetic material causes movement of the photoelastic objects when a magnetic field is applied to the photoelastic objects.

Other objects, such as lenses, prisms, polarizing films, quarter or half wave plates, springs and other objects may be embedded within the substrate for a similar effect. The magnetic objects may be embedded already magnetized or as unmagnetized metallic objects that are magnetized after being embedded. Polarizing films may be grafted onto regular or irregular plastic, glass, or Plexiglas shapes by cutting the film to size or by grafting the actual polarizing dye onto the shape.

Edible photoelastic objects that may be gelatin based or made of any other edible material may also be developed. As an example, a recipe may contain a mixture of gelatin, minimal water content, an artificial sweetener, and an optional flavoring. The mixture is heated, cooled and dried out. The final objects may be any size, shape, or color. They may be any degree of translucency, transparency, and degree of flexibility. The objects may also be enhanced with vitamins or minerals. The edible forms add amusement, learning and exploration to the eating experience. A further benefit is the increase in time for consumption adding health benefits. Moreover, the use of products such as gelatin creates a low or no carbohydrate snack if no sugar or carbohydrate flavorings or sweeteners are used. Slow consumption and lower carbohydrate intake have potential health benefits in behavioral management of obesity, diabetes and lipid levels. The edible photoelastic shapes may also be designed as puzzles or building kits.

A light source may be included as part of the toy polariscope. The light source can project an image or images from the observed object or objects between the polarizing films onto a screen that may also be a part of the device.

A plank or rod-like structure is attached to the polarizing films. The plank or rod-like structure may have grooves or other means to place other fixtures, such as mirrors, lenses, quarter and half wave plates and devices for holding objects in various positions of deformation. The polarizing films are detachable from the plank or rod and may be replaced with other devices for observing optical phenomena. For example, a mirror may replace one of the polarizing films so as to observe photoelastic stress patterns by reflection. Still further, objects that already have a mirrored surface as part of the objects may also display this effect. The screen and light fixtures may be detachable from the plank or rod-like structures for greater flexibility. The device is constructed so that it may be used with the plank or rod-like structure holding the polarizing films and/or with other fixtures in a horizontal or vertical position.

The present invention may be constructed in a variety of sizes. However, in a preferred embodiment, a smaller device is held in a hand held tube or cone shaped form. Small instruments for manipulating small objects are included. A battery-operated light is located at one and/or both ends of the device and a detachable screw on cloth like cap attached to the opposite end is used as a screen. The screen is removable for direct observation. Small photoelastic objects can be any shape, such as, but not limited to, insects, plants, fossils, or rock shapes. A number of versions may be constructed including an open format or individual hand held disks with handles, etc. A format for viewing gelatin-based edible forms of photoelastic objects allows for sanitary manipulation and viewing prior to consumption.

Photoelastic objects that function as transparent, translucent and photoelastic candles are described. Devices stress photoelastic candle material to facilitate photoelastic effects. Candleholders provide functions of a polariscope with well placed polarizing films, other optical films and devices. Reflective surfaces may be included or the photoelastic candle material may have polarizing layers directly on its surfaces. The candle material itself or the wick may produce scintillation in the flame or other optical effects due to chemical or other elements within or around it. Materials or objects may likewise be embedded in the candle material or on its surfaces for optical or other effects such as reflection from the flame, diffraction, magnification, focusing or dispersion of light. Optional scents may also be applied.

Edible forms of photoelastic or non-photoelastic candle material may be developed such that solid as well as melting portions may be consumed.

The present invention also includes a kaleidoscope of photoelastic displays. The kaleidoscope may be battery powered and have a light source and a motor for turning the display. Manuel manipulation and use of ambient light is also an option. The display has a stressed photoelastic piece or pieces sandwiched between polarizing films, or a mirror and a polarizing film or films. Mechanical manipulation may also be used. The device may be a flashlight-type device for projecting images on a wall or screen.

In another embodiment, a photoelastic object is mounted on an axel like device between two rotating polarizing films. An axel like device may have other films and devices on the axel for creating complex images.

In another embodiment, a box may be used to hold a photoelastic object. The box may include a light source. The photoelastic object is manipulated by screws or other devices extending into the box.

The present invention is a method of creating photoelastic objects or photoelastic films on objects. One method requires a user to pour prepared contents on a nonstick surface. The material is then cured and desired shapes are cut from the cured material. The objects may be edible or non-edible. The prepared contents may also be poured into molds.

In another method, an object is placed in a liquid. A polarizing material is placed on the top of the liquid and oriented. The liquid is then removed, leaving an oriented film on the coated object. Other sides of the object may then be coated with films. Alternatively, layers of materials that are optically active polymers may be stretched into desired forms. Edible polarizing films may be made of plasticized sugar, starch, gelatin with a non-toxic chiral dye or light absorbing optically active chemicals like gold, silver, iodine, hydrocarbons, certain vitamins, lipids, phospholipids, carotenoids, amino acids, lecithin, alcohols, potassium chloride or sorbate, sodium bicarbonate or benzoate, glycine, glycerine, or dicalcium, etc.

Other photoelastic objects are shaped as dolls or figurines. The objects are photoelastic in part or in whole and may have non-photoelastic counterparts. The objects may be designed such that only parts of the device are photoelastic. As an example, eyes on a doll may be photoelastic.

The present invention is also a kit for making photoelastic objects or accessories, particularly, edible photoelastic objects and accessories. Accessories may include lenses, fiber optics, filters, mirrors, prisms, etc. Pre-made edible supplies may also be provided.

The purpose of the present invention is to amuse as well as to stimulate an interest in science and engineering in children and adults.

These and further and other objects and features of the invention are apparent in the disclosure, which includes the above and ongoing written specification, with the drawings.

BRIEF DESCRIPTION OF THE DRAWINGS

FIG. 12 shows molds for casting plastic.

FIG. 13 shows molds for casting plastic.

DETAILED DESCRIPTION OF THE PREFERRED EMBODIMENTS

The present invention includes a variety of toy polariscopes that are simpler in design and less costly than the precision instruments used in scientific research and stress analysis of materials and structures. These toys allow children and adults to explore and observe photoplastic and photoelastic stress patterns in various objects. Objects that may exhibit these properties are glass, plastic, Plexiglas, candle gel or wax material and even edible photoelastic objects. Other optical phenomena may also be observed, such as optical phenomena in the sky.

Figure 1:
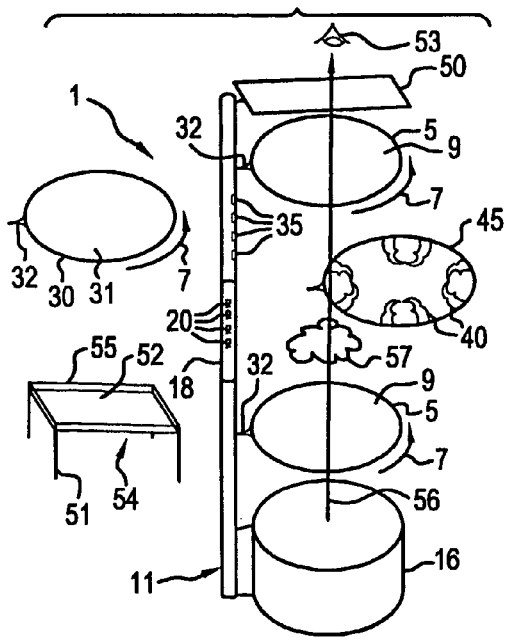
FIG. 1 is a side view of a toy polariscope.

FIG. 1 is a side view of a toy polariscope 1. The polariscope 1 may be of any size. Detachable fixtures 5 on a plank or rod structure 11 hold polarizing films 9. The number of detachable fixtures 5 may vary depending on the particular embodiment. The detachable fixtures 5 allow rotation 7 perpendicular to a central axis of the polariscope 1. This rotation controls the transmission of light 56 through the polarizing films 9. The plank or rod structure 11 holds fixtures in a set position. The plank or rod structure 11 may be held in either a vertical or horizontal position. An insert 18 may be provided to extend the length of the plank or rod structure 11. Holes 20 on the insert 18 with screws allow for fixation of various lengths of the plank or rod structure 11.

A light source 16 serves as either projecting light or diffuse light. The light source 16 may be detached and reattached from the plank or rod structure 11 as needed. Light may lie in a horizontal position and support a vertical position plank or rod structure 11 with its contents or sit vertically to project through a horizontally placed plank or rod structure 11 with its contents.

Another fixture 30, similar to the detachable fixtures 5, houses a quarter or half wavelength plate, mirrors, filters, lenses or other devices 31 for optical effects. More than one of these additional fixtures 30 may be used with one or more types of optical devices 31. Inserts 35 on the plank or rod structure 11 hold the additional fixtures 30. As an alternative to the inserts 35, the fixtures 5, 30 may be attached to the plank or rod structure 11 by means of fastening devices 32 attached to the fixtures 5, 30. Alternatively, fixtures 5, 30 may glide along the plank or rod structure by insertion into groves along its length.

Another type of fixture 45 allows for placement of photoelastic objects 57 in various positions of deformation. The fixture 45 has clamps 40 or other tools to hold, compress, stretch, deform, and/or otherwise manipulate a photoelastic object 57 in various positions of deformation. The clamps 40 may also hold other objects, such as lenses, mirrors, films, etc. Furthermore, there may be more than one of this type of fixture 45 on each polariscope 1.

A screen 50 may be used to view projected images. Images may be viewed on either side of the screen 50. The screen 50 may also be detachable for direct viewing. Other possible parts of a polariscope include a stand 54 to hold an object or objects. One or more stands 54 may be stacked, attached or otherwise connected together. The stands 54 themselves may be of various shapes and configurations, and may include hooks, frames, platforms and other devices to interplay with other objects displayed on the stand 54. The stands 54 may also be photoelastic. In a preferred embodiment, the stand 54 has a platform 52, legs 51, and a raised barrier 55 to prevent spherical or other mobile objects from falling or rolling off the stand 54.

Unpolarized light 56 travels from the light source 16 through a first fixture 5 polarizer, through a photoelastic object 57, and then through a second fixture 5 polarizer to an observer 53. The observer 53 may view projected fringes on either side of the screen 50 or directly without the use of the screen.

Figure 2:
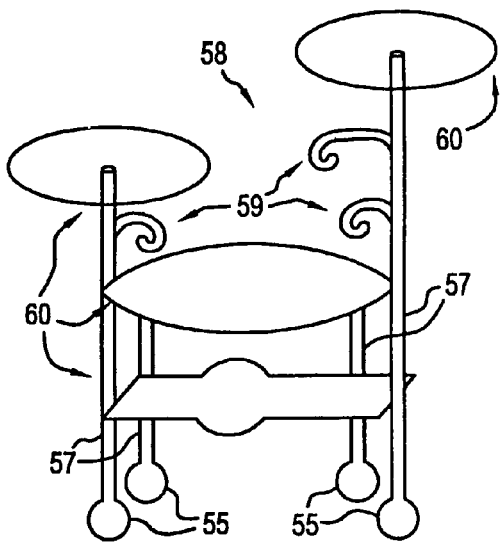
FIG. 2 is a perspective view of a stand for holding objects during observation.

FIG. 2 is a perspective view of a stand 58 for holding objects during observation. The stand 58 may be designed with multiple areas 60 for placement of objects or may have hooks 59 for hanging objects. The stand 58 may be made of photoelastic or photoplastic material that is pre-stressed to contribute to the photoelastic display. Some parts of the stand 58 may be detachable and reattachable in various configurations. Feet 55 rest on a surface and support legs 57.

Figure 3:
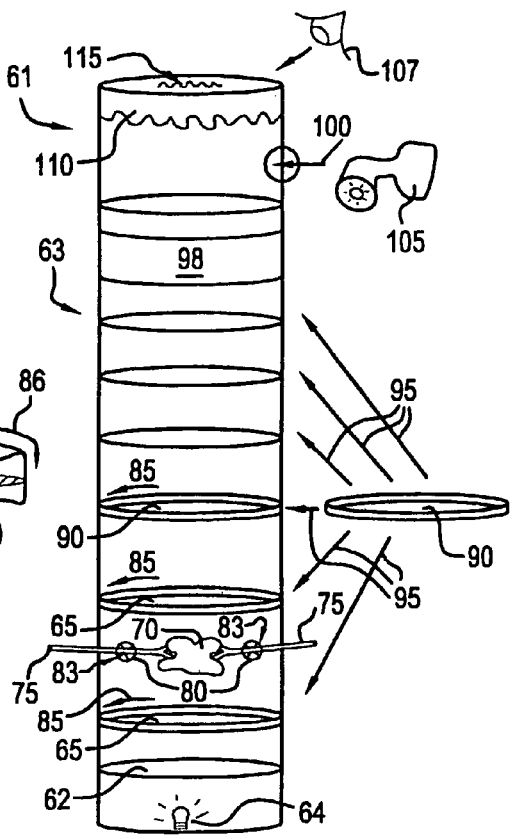
FIG. 3 is a side view of another embodiment of a toy polariscope.

FIG. 3 is a side view of another embodiment of a toy polariscope 61. At the base of the polariscope 61 is a detachable screw or snap on compartment 62 with a battery operated light 64. A hollow tube or cone shaped structure 63 provides a frame for all attachments and inserts. Inserts 65 hold polarizing films that are free to rotate 85 perpendicular to a central axis of the polariscope 61. A user rotates 85 the inserts 65 with fingers, tools or other attachments.

Photoelastic objects 70 are observed. The photoelastic objects 70 may be of any shape, including, but not limited to fantasy shapes or shapes resembling real world objects. Tools 75 may be included for holding and manipulating the photoelastic objects 70. In a preferred embodiment, two pincher-like tools 75 for grasping are inserted into the hollow tube or cone shaped structure 63 through one or more holes 80. A fixation device 83 allows the tools 75 to be rigidly fixed in place. This frees the user's hands and allows the user to view the photoelastic effects of deformation. One or all of the tools 75 may be fixed, while other tools 75 are used to manipulate the object. The tools 75 may have sharp points or blunt ends to create various deformation effects. Each hole 80 may be opened to fully insert and move around the tools 75, loosely hold tools 75 in place with slight friction or rigidly hold the tools 75 in a fixed position.

Other inserts 90 may contain other devices, such as quarter or half wave plates, mirrors, filters, lenses or other optical devices that function like the inserts 65. The other inserts 90 are inserted, rotated and placed anywhere an insert space 95 is provided. Larger spaces 98 may be provided in the chamber 63 for larger optical devices, such as larger mirrors, lenses, prisms, crystals, etc. Note that lenses and mirrors may be any kind, including convex and concave or fresnel lenses. The larger insert 98 may be removed for placement of optical devices and re-inserted.

The polariscope 61 may also have an opening 100 for insertion and fixation of a battery operated light 105 on an upper part of the chamber for observation of photoelastic properties by reflection. The lower light source 62 is more suitable for observation of photoelastic objects by transmission. The opening 100 may be plugged when a light 105 is not in place. While this embodiment describes a battery operated light, an electrical connection is also an option.

The polariscope 61 includes a screw or snap on screen 110 to allow a user 107 to view projected images 115 generated by either transmission or reflection. The user may also observe the images directly by removing the screen and looking directly into the chamber.

Figure 4:
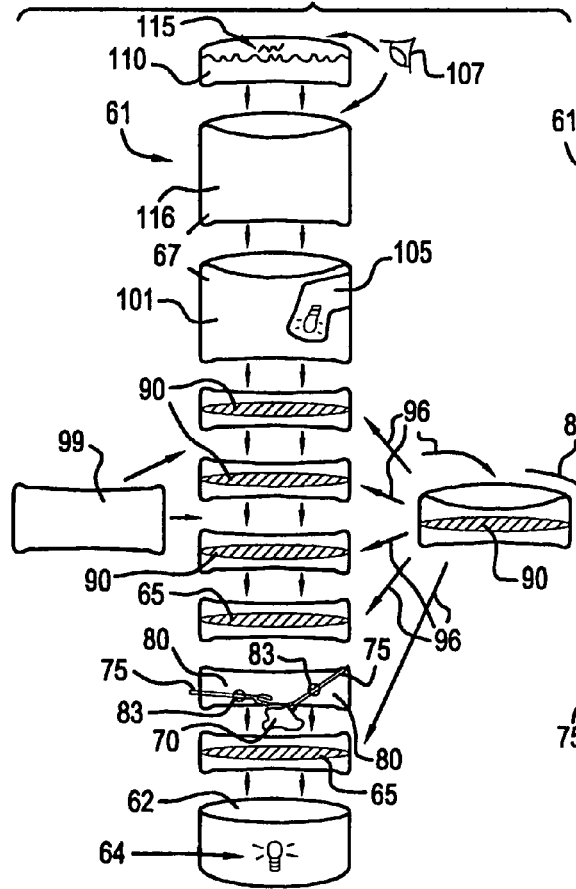
FIG. 4 is a side view of a toy polariscope showing assembly and disassembly.

FIG. 4 is a side view of a toy polariscope 64, similar to the polariscope 61 of FIG. 3, showing assembly and disassembly. Individual compartments 96 have snap on connections 67 that allow for rotation 86 of the compartments 96 perpendicular to the central axis of the polariscope 64. The individual compartments 96 may be detached from one another and reassembled in any order. Inserts 90, 65 may also be removed and interchanged with other compartments 96. A larger compartment 99 for larger optical objects is also detachable. A special compartment 101 may contain a light 105 and is detachable like the other compartments 96, 99. A blank compartment 116 may be added as a base for assembly.

Figure 5:
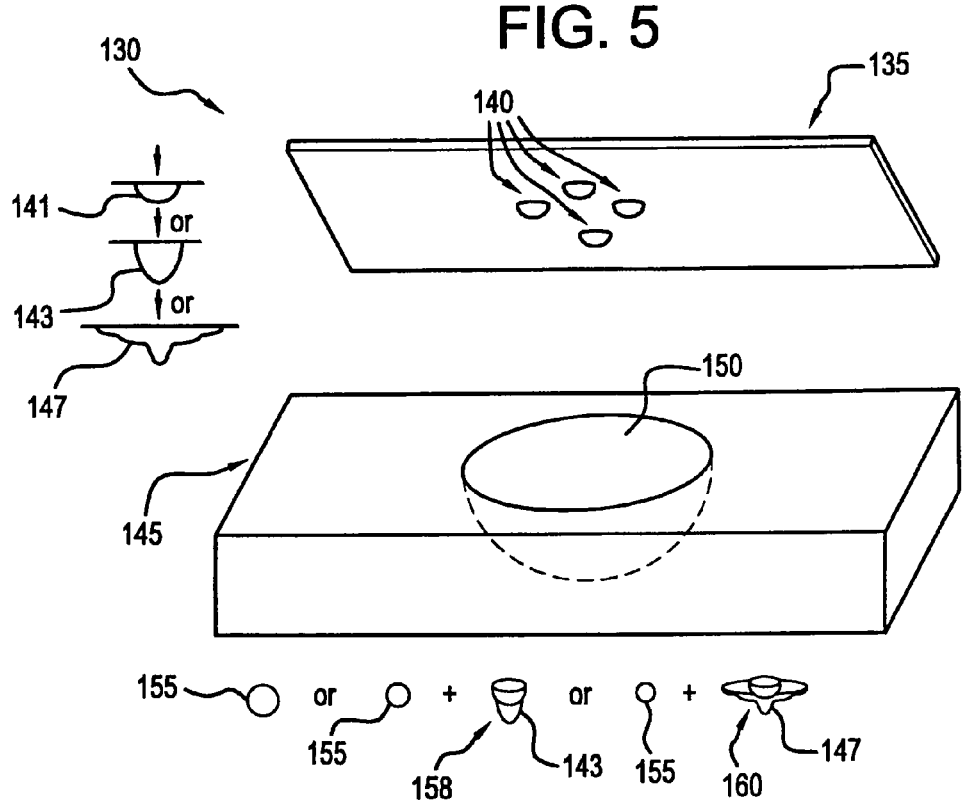
FIG. 5 shows a casting process for embedding objects within photoelastic plastics.

FIG. 5 shows a casting process 130 for curing plastic photoplastic/photoelastic shapes. A lid 135 covers plastic in an impression 150 in a mold 145. The mold 145 is preferably made of Teflon. The impression 150 may be of any shape. FIG. 5 shows a spherical impression 150. To make a complete solid, two similar halves are pressed together in a semi-polymerized state. The lid 135 may have additional, smaller impressions 140 to create placements for embedded objects 155, such as magnets. The smaller impressions 140 may be of any shape, but are preferably slightly smaller than the objects 155 to be implanted. The smaller impressions 140 may be rounded 141, pointed 143 or a combination thereof 147. Prior to fixing the two halves together, the objects 155 are inserted into the smaller impressions 140, the photoelastic material stretches and creates enhanced stress patterns. If magnets are used, they may be pre-magnetized or magnetized after the casting process 130. In a preferred embodiment, spherical magnets 155 may be fitted into cone shaped objects 158 or star shaped objects 160.

Figure 6:
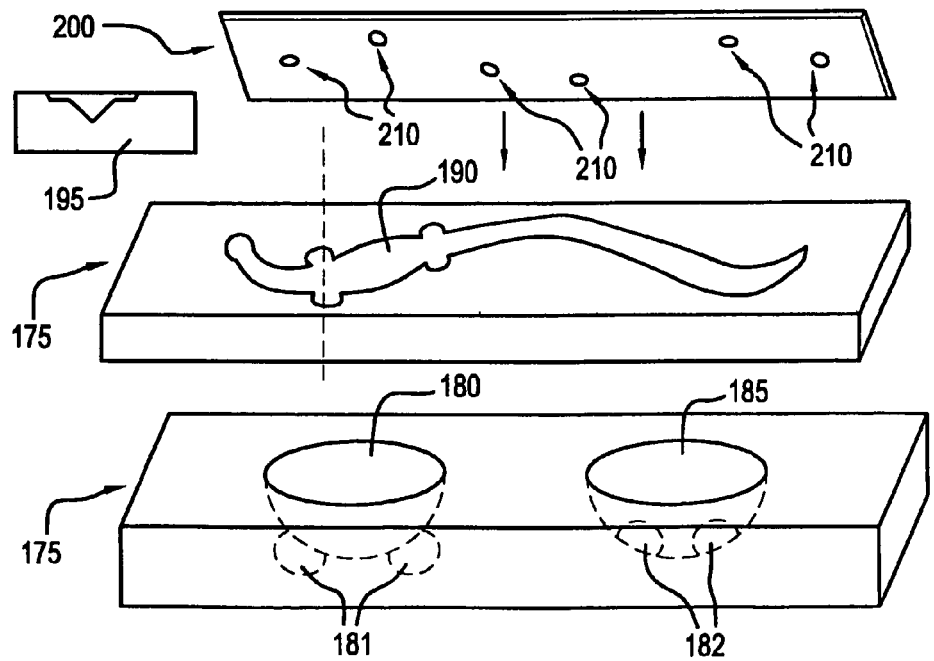
FIG. 6 shows various other types of casting molds.

FIG. 6 shows various other types of casting molds 175. The molds 175 are preferably made of Teflon. In one embodiment, a half sphere 180 has small spherical impressions 181 and another half sphere 185 has small spherical indentions 182. The two halves 180, 185 may be combined with a similar half or an opposite half. In another embodiment, a cast is made in the form of a lizard or worm 190. This may be simply a wavy half cylinder impression in which a lid 200 with small protrusions 210 to create impressions may be placed over it on the casted plastic for creation of space for placement of embedded magnets or other objects when the two halves are brought together. A cross section 195 shows varying depths of the mold 175 when a lizard or worm shape 190 is being made. As mentioned, a lid 200 forms other impressions 210. FIG. 6 shows a staggered set of impressions 210 for creating impressions in a wavy cylindrical shape.

Figure 7:
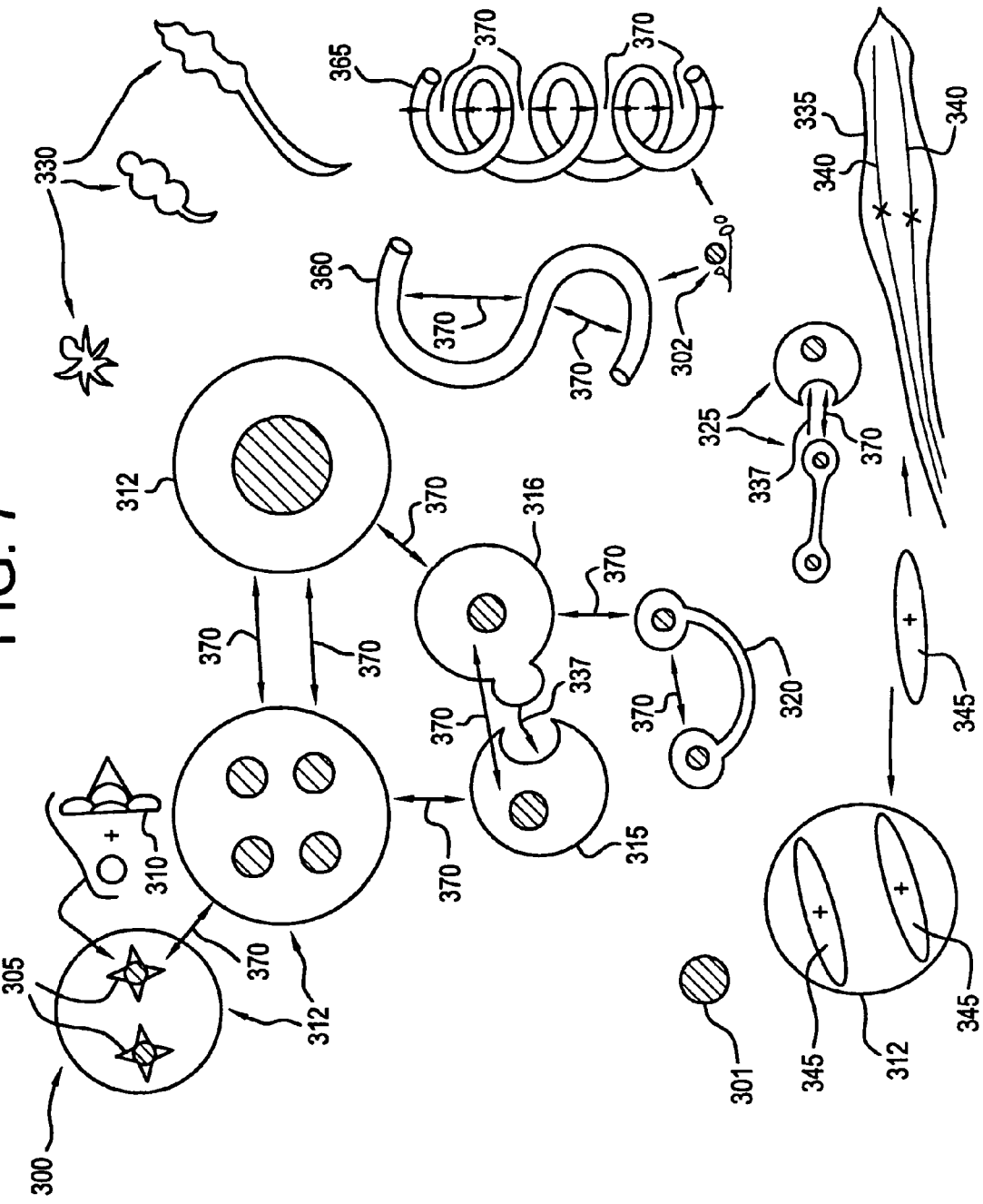
FIG. 7 shows a variety of forms of casted photoelastic objects and interactions.

FIG. 7 shows a variety of forms of casted photoelastic objects 300 and interactions. Different shapes 300 may interact by magnetic attraction 370 and by insertion 337 of one shape into another. Photoelastic objects 300 may have embedded spherical magnets 301, 302, and 305 with fitted star shaped coverings or fitted cone-like coverings 310 whose points make more significant fringes when the magnets move towards or away from one another due to magnetic attraction with magnets within an object or with magnets in other objects or simply by manual manipulation. A spherical object 312 may have zero, one or more magnets embedded. Other objects 315 may have inward facing pouches or objects may have outward facing pouches 316. This allows for objects 316 to be inserted 337 into objects 315. Objects may be dumbbell shaped 320 with embedded magnets that pull ends together. This causes deformation by bending and creates more fringes. Various shapes may interact 325 in various ways (i.e. 337, 370). Objects may be creature shaped 330 to add entertainment value. Circular 345 or other shaped polarizing film 340 may be embedded at opposite ends of a spherical photoelastic object 312 or other shaped object 335. In cylindrical photoelastic objects 360, magnetic attraction 370 causes the shape 360 to fold on itself. The folding may create a helical shape 365 that can be extended or enlarge by attaching other objects 365.

Figure 8:
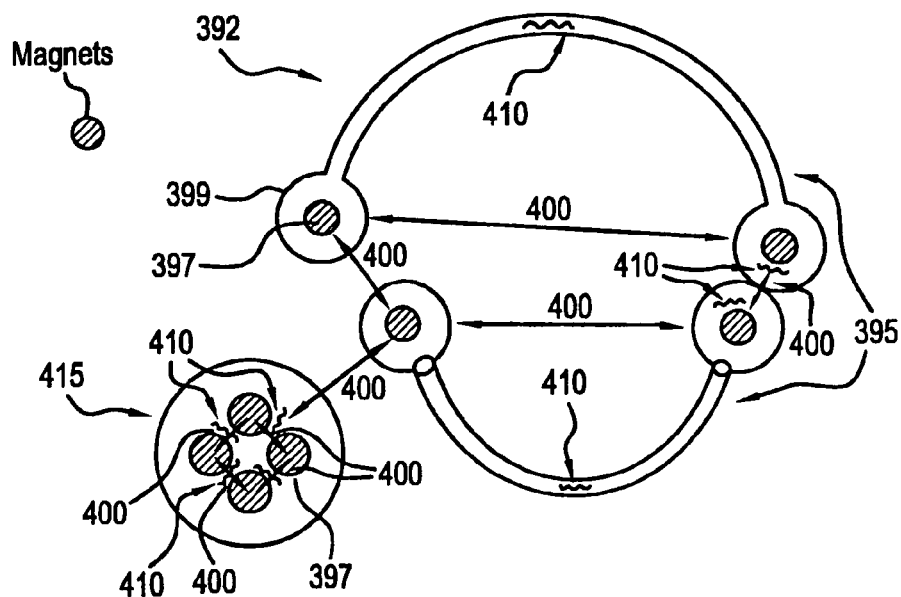
FIG. 8 shows interactions between photoelastic shapes.

FIG. 8 shows interactions 400 between photoelastic shapes 392. Various shaped objects may be used. Dumbbell shaped objects 395 may have magnets 397 embedded in spherical ends 399. The magnets attract or repel 400 one another creating fringe patterns 410 as a result of stress and compression. A spherical photoelastic object 415 may have four embedded magnets 397 and fringes 410 caused by compressive forces 400 on the material generated by the magnets 397.

Figure 9:
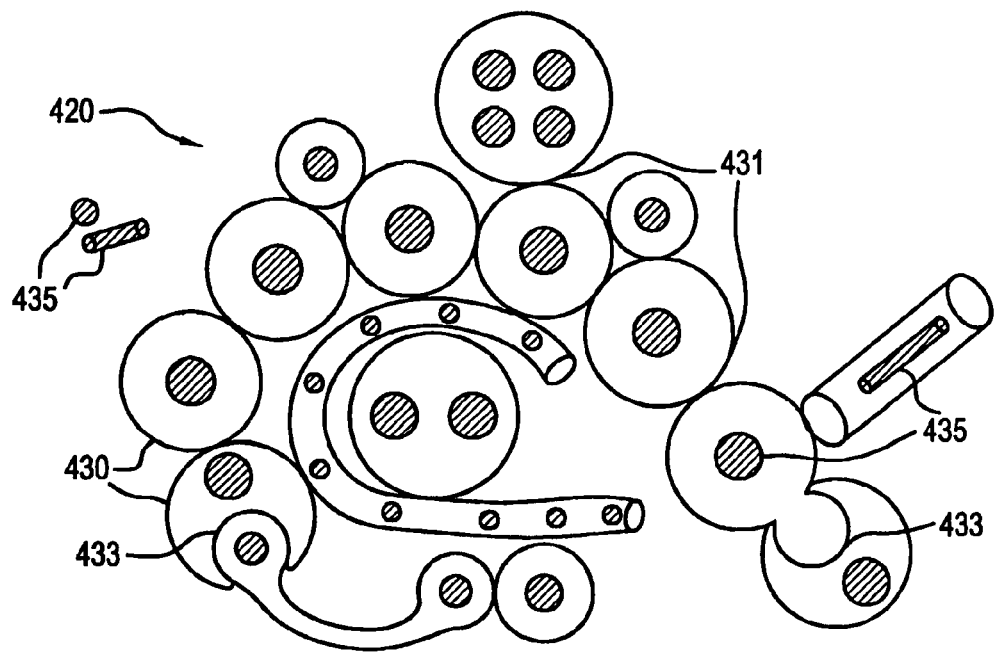
FIG. 9 is a diagram of a possible configuration of interacting photoelastic objects.

FIG. 9 is a diagram of a possible configuration of interacting photoelastic objects 420. The objects 430 may be in contact 431 with one another due to magnetic forces or other devices or inserted 433 into one another to create a display. Magnets 435 of a variety of shapes may also be included to create visual effects.

Figure 10:
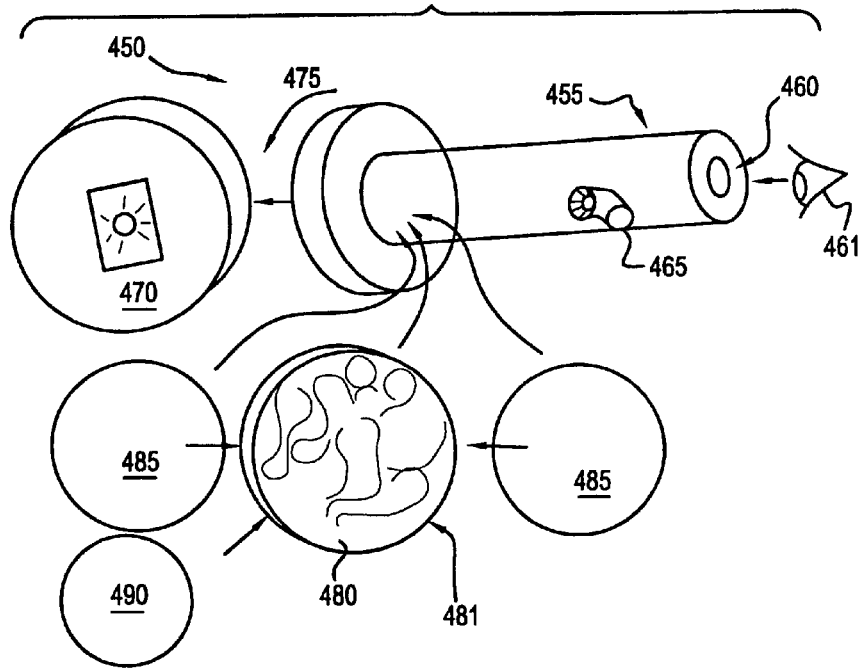
FIG. 10 shows a photoelastic kaleidoscope.

FIG. 10 shows a photoelastic kaleidoscope 450. The body of the kaleidoscope 455 may be cylindrical or another shape. A viewing port 460 allows a user 461 to see into the kaleidoscope 450. Several lighting options are available. A light source 470 may be provided outside or attachable onto the kaleidoscope 450 for viewing photoelastic effects by transmission or an alternate light source 465 may be provided for viewing photoelastic effects by reflection. A compartment 481 is rotatable 475 between two polarizing films 485 or between a polarizing film 485 and a mirror 490. The compartment 481 may be turned 475 manually or with a motor. A part 480 of the compartment 481 contains photoelastic material that is stressed and arranged for making fringes and may be accessed with tools or devices to alter the stress patterns. Polarizing films 485 and/or a mirror 490 are held in place by devices that allow rotation perpendicular to the central axis of the body of the kaleidoscope 455. This allows for control of the transmission of light. Light may be transmitted from a light source 470, through a polarizing film 485 below part 480, through part 480 containing stressed photoelastic material, through a polarizing film 485 above part 480, through the kaleidoscope body 455, out the port 460 and to the observer 461. Alternatively, a mirror 490 below part 480 receives light from light source 465 and reflects it back through part 480 containing stressed photoelastic material and through a polarizing film 485 above part 480, through the kaleidoscope body 455, out the port 460 and to the observer 461.

Figure 11:
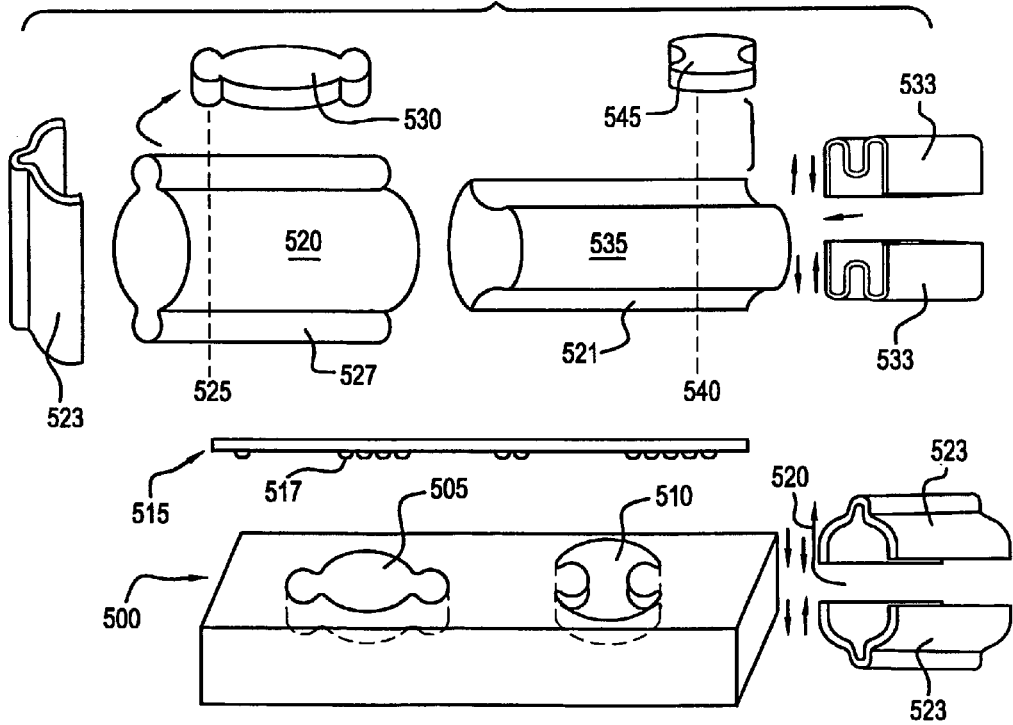
FIG. 11 shows molds for casting plastic.

FIG. 11 shows molds 500 for casting plastic. A mold 500 may have opposing impressions 505, 510. These may form spherical shapes with smaller out pouches or in pouches or similar cylindrical shapes. A lid 515 has half-spherical or other shaped impressions 517 to create space for embedding magnets and/or other objects into opposing impressions 505, 510. Alternatively, a long cylindrical photoelastic plastic object 520 with smaller cylindrical out pouches 527 is cast between two half cylindrical molds 523. Corresponding long cylindrical photoelastic plastic object 535 with smaller cylindrical in pouches 521 is cast between two half cylindrical molds 533. Precast 520 is poured into two of the molds 523. The molds 523 are bound together to form a hollow tube that can be separated once the plastic is cured. The objects 520, 535 may be sliced 525, 540 perpendicular to the central axis to create slices 530 and 545, respectively. The slices 530, 545 interlock, causing stretching and compressing that results in fringes.

FIG. 12 shows molds 560 for casting plastic. In one embodiment, a half cylindrical impression 565 with tapered ends is used to cast a full cylinder when the two halves are brought together. A lid 570 covers the plastic mold 560 and leaves impressions 571 of half spherical shapes for insertion of magnets into a complete cylindrical object when two halves are brought together. In another embodiment, a wavy half cylindrical impression 575 with tapered ends is used to cast a full cylinder when the two halves are brought together. A lid 580 covers the plastic mold 560 and leaves impressions 581 of half spherical shapes for insertion of magnets into a complete wavy cylindrical object when two halves are brought together.

FIG. 13 shows a mold 590 for casting plastic. A dumbbell shaped cylindrical impression 595, with a thin body 597 and spherical ends 599, is used to cast a full cylinder and full spherical ends when the two halves are brought together. A lid 600 covers the plastic mold 590 and leaves impressions 601 of half spherical shapes for insertion of magnets into a complete dumbbell shaped cylindrical object when two halves are brought together. A horizontal view 605 of lid 600. is shown.

Figure 14:
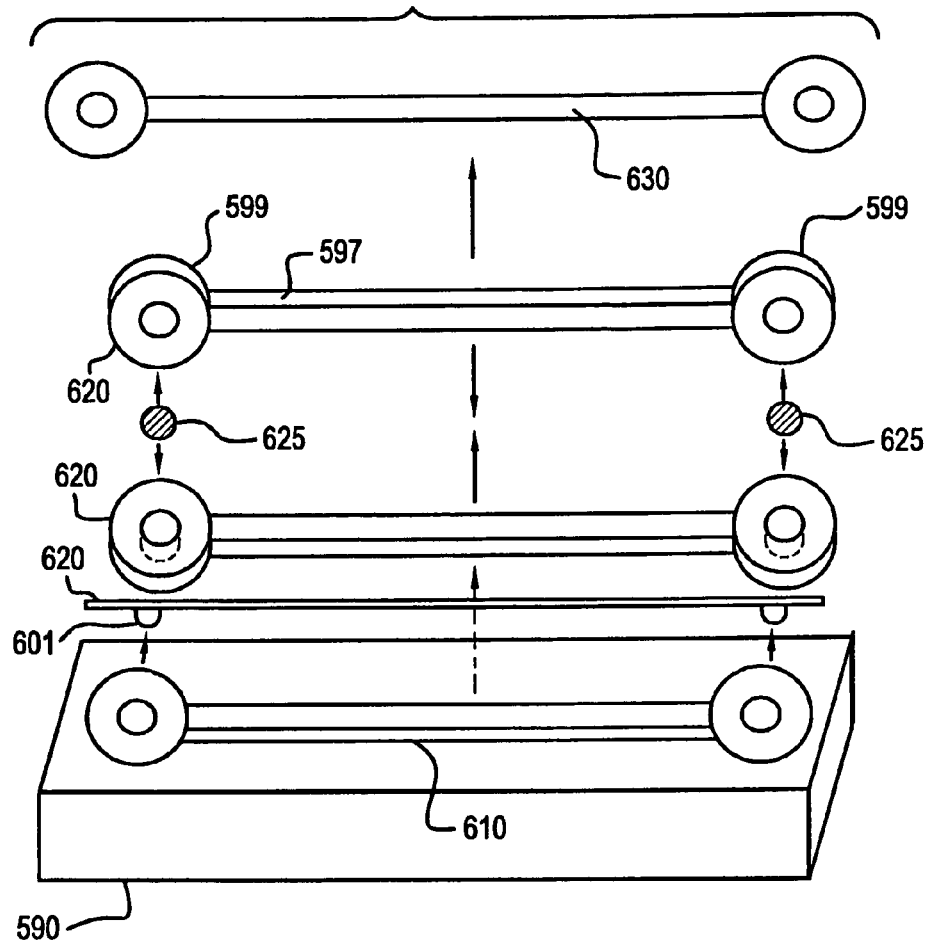
FIG. 14 shows a dumbbell shaped plastic mold.

FIG. 14 shows a dumbbell shaped plastic object 610. The dumbbell shaped object 610 is removed from the mold 590 and two halves are brought together 620 around embedded spherical magnets 625 to create a final object 630.

Figure 15:
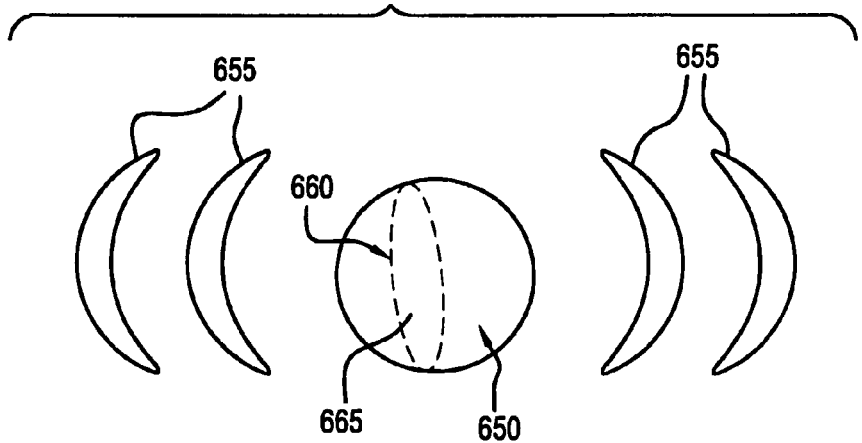
FIG. 15 shows a spherical photoelastic object with tailored polarizing film.

FIG. 15 shows a spherical photoelastic object 650 with tailored polarizing film 655. The pieces of polarized film 655 are placed 660 on the spherical object 650 in predetermined positions 665. The polarizing film 655 may be edible or inedible.

Figure 16:
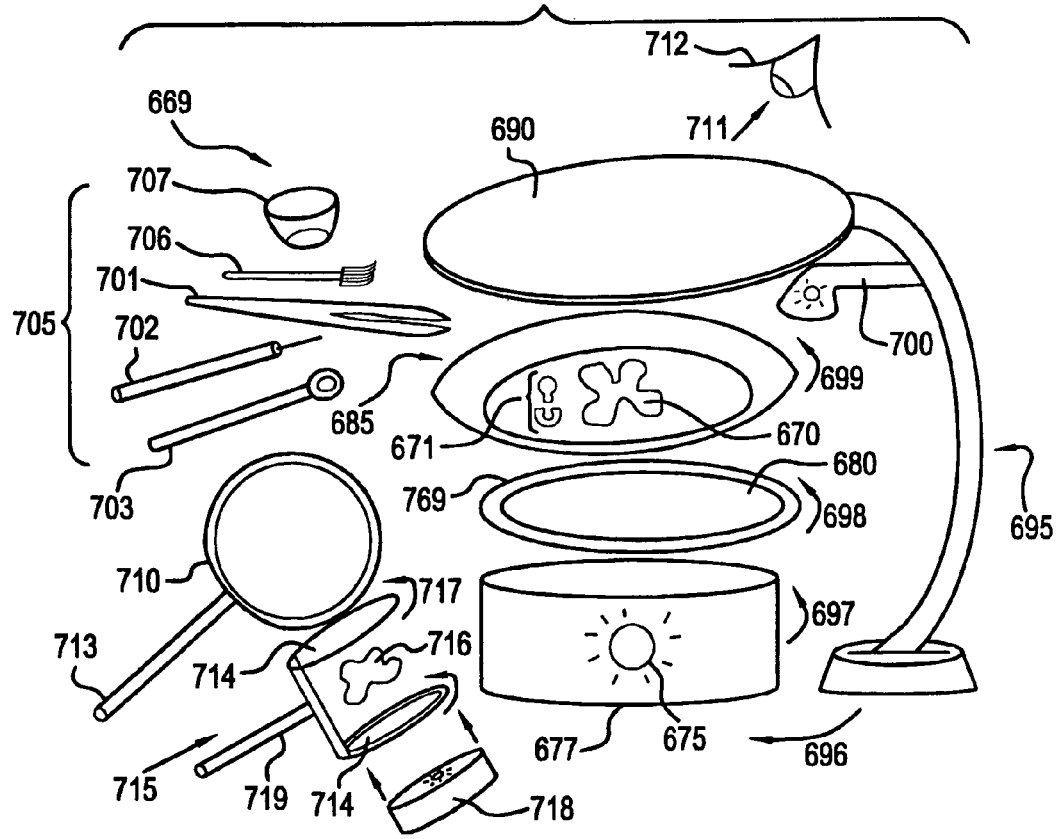
FIG. 16 shows a toy polariscope device for observing edible photoelastic objects.

FIG. 16 shows a toy polariscope device 669 for observing edible photoelastic objects 670, 671. The edible photoelastic objects 670 may be observed and/or eaten and may be formed into interlocking shapes 671, such as puzzles or building blocks. The objects 670, 671 may have a stickiness when water is applied, providing means for sticking objects together. A light source 675 within a compartment 677 may be polarized or unpolarized. A frame 679 holds an optical film 680, such as polarizing film, half or quarter wave plates, filters, mirrors, fresnel or other lenses, other optical devices or combinations thereof. Frame or frames 679 are attached to the light source compartment 677 or placed above the light source or above or below dish 685. The dish 685 is a translucent, transparent or mirror reflective dish where the objects 670, 671 are placed. The dish 685 may also have a polarizing film incorporated into it away from the surface exposed to edible material or to physical handling. The dish 685 may have fixed photoelastic properties that add to the display. A user 712 may rotate 697 the compartment 677 holding the light source 675, rotate 698 the polarizing film 680 or rotate 699 the dish 685. This is to facilitate control of the transmission of light 711. Toy polariscope 669 as well as other embodiments may be edible or inedible in whole or in part.

A stand 695 may be bowed to allow minimal obstruction to user's hands and the placement of the dish 685. The stand 695 may be moved 696 in a circular path to control orientation of a mounted optical film 690, which may be a polarizing film with respect to another polarizing film 680 for controlling the amount of light 711 reaching an observer 712. The mounted optical film 690, such as polarizing film, half or quarter waveplates, filters, mirrors, fresnel or other lenses, or other optical device, is located on the top of the stand 695. The mounted optical film 690 may be replaced with polarized glasses on the observer 712. The glasses may have other optical devices as well. A polarizing light source 675, a first polarizing film 680, and the dish 685 may be rotated with respect to the mounted optical film 690. An alternate light source 700 may be used for observation by reflection off a mirrored surface on or below the dish 685.

Various instruments 705 allow the user 712 to hold, pull, stick, press and/or squeeze the photoelastic objects 670, 671. Instruments 705 may include tweezers 701, sharp instruments 702 or blunt instruments 703. A brush 706 may also be provided to add water or syrup or other substances to surfaces of the objects 670, 671 to make the objects 670, 671 sticky and capable of adhering to other objects. A cup 707 for water may also be provided along with other edible substances, such as, but not limited to, honey, syrup, or other flavorings. These substances may also be provided.

An alternative method of mounting optical devices, such as polarizing films, mirrors, quarter and half wave plates, filters, lenses, fresnel lenses, etc uses a circular mount 710 attached to a handle 713 for the observer 712 to hold. This device may hold one or more optical devices that can rotate with respect to one another and can be used to observe the sky. This may likewise be an edible polarizing disc made of edible plasticized sugar and other edible optically active chiral chemicals and polymers mounted on a stick like a lollypop 710, 713. Light from a light source 718 provides illumination in dimly lit areas. The light travels up from the light source 718 and through a device 715 with two polarizing films 714 attached to a handle 719. A photoelastic object 716 is placed between the two polarizing films 714. The user 712 may hold the handle 719 with one hand and manipulate the object 716 with the other hand. The polarizing films 714 rotate 717 with respect to one another.

Mixing, casting and play stress analysis kits may accompany this embodiment or the other embodiments using edible and/or inedible materials. For example, pre-cast mixtures or materials may be made for pouring into molds that form a variety of shapes or even cast onto a variety of mirrored shapes to play like real stress analysis is being performed.

Other embodiments may include forms with optical films mounted in stackable devices such as polarizing films mounted on devices with legs that fit on top of each other. This format can allow films to be rotated with respect to one another as the legs insert into a continuous groove or a series of holes through which to rotate or reinsert the legs.

Other edible, photoelastic embodiments are possible. Edible photoelastic objects may be cut or molded into various shapes and designs. The objects may have various flavors or colors and the objects may be hard or gummy. The packaging of the edible photoelastic objects may substitute for the toy polariscope. The packaging may contain polarized films, highly reflective surfaces or other optical devices. The edible photoelastic objects are observed through the packaging, with the fringes visible.

Figure 17:
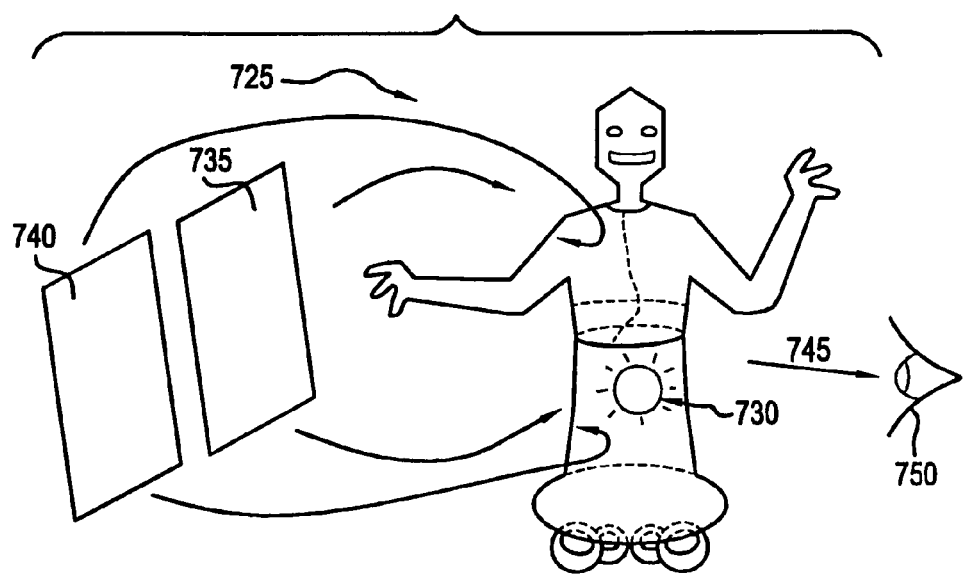
FIG. 17 shows a photoelastic object with an enclosed light.

FIG. 17 shows a photoelastic object 725 with an enclosed light 730. The object 725 may be a toy, such as, but not limited to, robots, dolls, or toy weapons made from translucent or transparent material with photoelastic and/or photoplastic properties. Photoplastic effects are formed when certain plastics, such as acrylic or polyurethane are stressed and/or unevenly heated and cooled during a curing phase. This leaves fixed fringes that may be viewed with polarized light. The light 730 is powered with a battery and may be designed to flicker or have a sustained emission. A polarizing film 735 is applied to the outer surface of the material and a polarizing film 740 is applied to the inner surface of the material. Light 745 travels from the interior of the object 725 through the polarizing film 740, through the material, through the polarizing film 735 and to an observer 750. If the polarizing films 735, 740 are not applied, the observer 750 may utilize a device similar to those previously described to observe fringe patterns.

Figure 18:
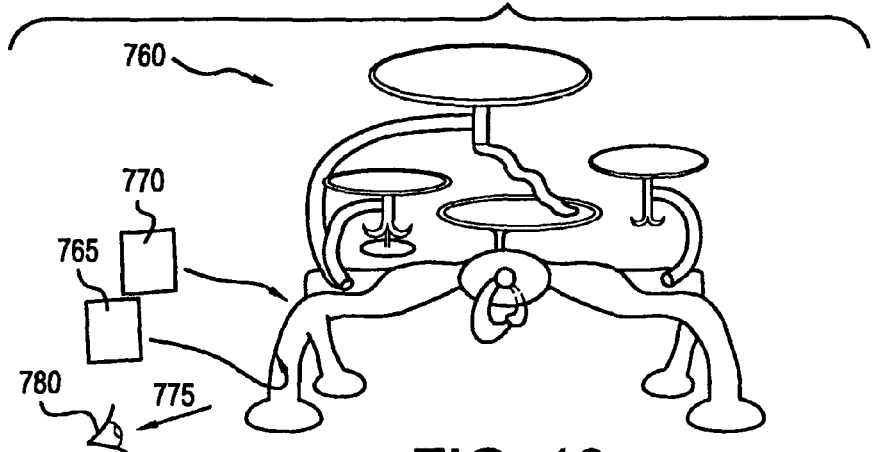
FIG. 18 shows a stand for observing photoelastic objects.

FIG. 18 shows a stand 760 for observing photoelastic objects. The stand 760 may either hold the photoelastic objects to be observed through a device previously described or be used to observe such objects with polarizing films attached to them as described previously. The stand itself may have photoelastic/photoplastic fringe patterns observed through a device previously described or have a polarizing film, dye or other polarizing device applied to an outer surface 770 and/or inner surface 765 of the material. Light 775 from an ambient source or another light source passes through the stand 760 and to an observer 780.

Figure 19:
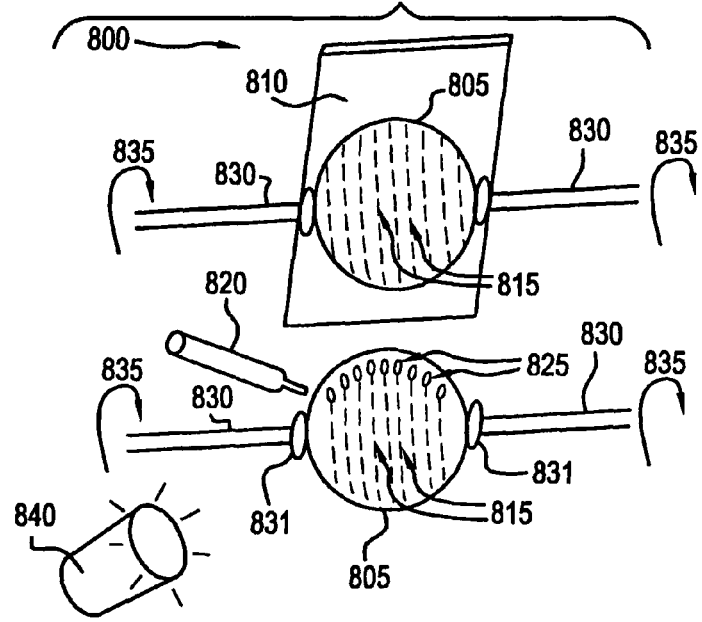
FIG. 19 shows a process for applying a polarizing film to a photoelastic object.

FIG. 19 shows a process 800 for applying a polarizing film to a photoelastic object 805. A buffing device 810 fits around the photoelastic object 805 and creates fine polishing grooves 815 in one direction on the photoelastic object 805. An applicator 820 applies droplets of dye 825 to the photoelastic object 805 and the dye 825 moves into the grooves 815. The dye 825 may be edible or inedible. The dye 825 is spread on the surface of the photoelastic object 805 by rotating 835 the photoelastic object 805 around on a fixation device 830. The photoelastic object 805 is held in place on the fixation device by stops 831. A heat source 840 facilitates drying of the dye 825.

Figure 20:
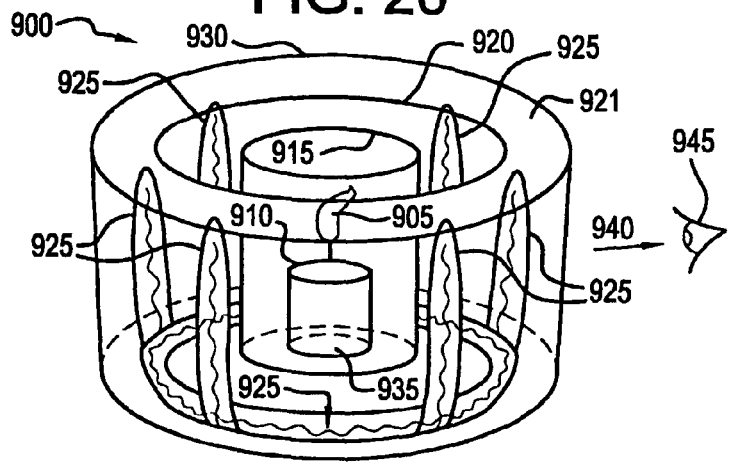
FIG. 20 shows a lamp or candleholder in a container.

FIG. 20 shows a lamp or candleholder 900. A light source 905 is either a candle flame or a light bulb. A candle 910 may be made of transparent, translucent, photoelastic or photoplastic materials that create fringe patterns when stressed. However, traditional opaque candles 910 may also be used. In a preferred embodiment, a protective glass barrier 915 surrounds the light source 905 to protect the plastic and polarizing films from heat. A first polarizing film 920 is attached to an inner surface of transparent or translucent glass, Plexiglas or plastic 921, which forms an open-ended enclosure around the light source 905. Transparent or translucent photoelastic material 925 is shaped into a cylindrical display between the first polarizing film 920 and a second polarizing film 930 on the outer surface of the glass, Plexiglas or plastic 921. The shapes 925 have fixed photoelastic fringes and may also change in display due to stress caused by heat, resulting in uneven expansion and contraction from a flame or lamp. The lamp or candleholder 900 may include a reflective surface 935 beneath the light source 905 to aid in visualization of the fringes from the candle 910 material itself if it is also photoelastic or it may simply enhance the visual effects of 925. Light 940 travels from the light source 905, through the barrier 915, polarizing film 920, glass, Plexiglas or plastic 921, the photoelastic material 925 within 921, the polarizing film 930 and to a user 945. Light 940 may also travel from the light source 905, through a translucent/transparent/photoelastic or even non-photoelastic candle material 910 and reflects off a reflective surface 935 back through the translucent/transparent/photoelastic or even non-photoelastic candle material 910 through polarizing film/films 920 and/or 930 as well as 921 and/or 925 to the observer 945.

Figure 21:
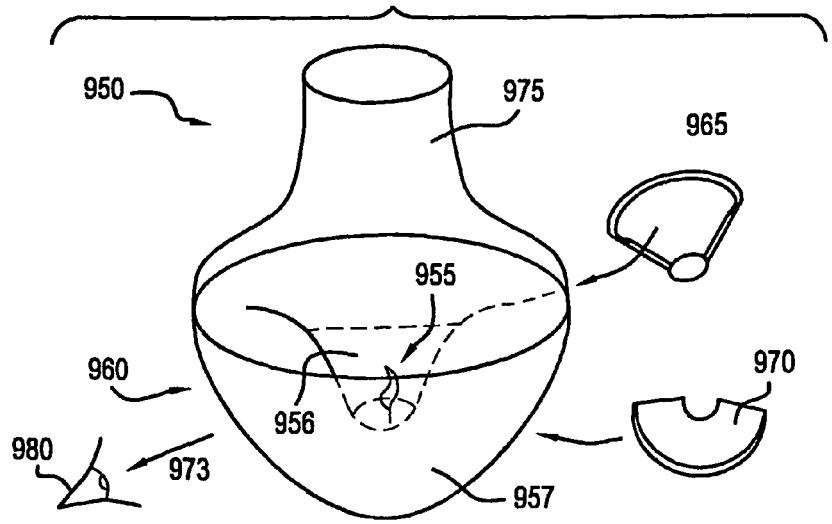
FIG. 21 shows a candleholder and candle gel or wax material with photoelastic properties.

FIG. 21 shows a candleholder 950 that is designed for transparent or translucent candles that are also photoelastic. Gel candles or candles formulated with other suitable materials may be specially formulated such that the candle material itself may display prominent photoelastic properties when stressed. A flame 955 provides illumination from within a depression 956 within candle material 957. A bowl shaped structure 960 holds the candle material 957 and is itself transparent or translucent. A mirrored surface 965 covers a portion or all of an inner surface of the bowl 960. A polarizing film 970 covers a portion or all of an inner and/or outer surface of the bowl 960. Light 973 from the flame 955 is reflected off the mirrored surface 965 and travels through the candle material 957, through the bowl 960 and polarizing film 970 and to a user 980. And open lid 975 may be provided whose inner and/or outer surface is covered with a polarizing film to provide another viewing angle particularly if the entire surface of the bowl 960 is covered with a mirrored surface 965. Light 973 from the flame 955 is reflected off the mirrored surface 965 and travels through the candle material 957, through the lid covered with polarizing material 975 to the observer 980. The user 980 may observe the candleholder 950 from various angles.

Figure 22:
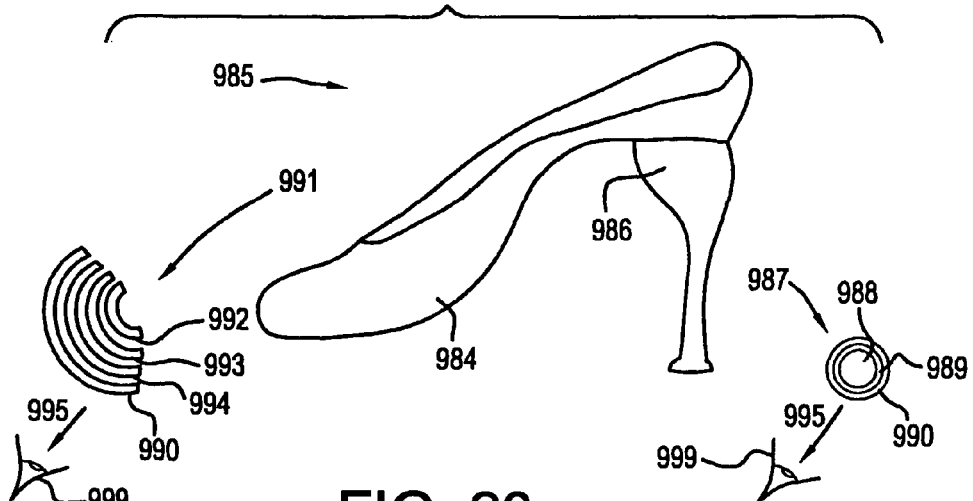
FIG. 22 is a side view of a shoe with photoelastic properties.

FIG. 22 is a side view of a shoe 985 with photoelastic properties. Part or the entire shoe may be made from photoelastic materials. In a preferred embodiment, a high heel 986 is made of transparent or translucent photoelastic or photoplastic material. A cross section 987 of the heel 986 shows an inner portion 988 with transparent or translucent photoelastic material, a polarizing film 989 circling the inner portion 988, and a protective transparent or translucent material 990 surrounding the polarizing film 989. The body of the shoe 984 may also be made of transparent or translucent photoelastic or photoplastic material. A cross section 991 of the body 984 shows a first layer of highly reflective material 992 visible from the exterior of the shoe 985, an inner portion 993 with transparent or translucent photoelastic material, a polarizing film 994 circling the inner portion 993, and a protective transparent or translucent material 990 surrounding the polarizing film 994. Ambient light 995 is reflected off the mirrored surface 992 and travels through the inner layer 993, polarizing film 994 and outer protective layer 990 before reaching a viewer 999. Light is transmitted by transmission or reflection.

Figure 23:
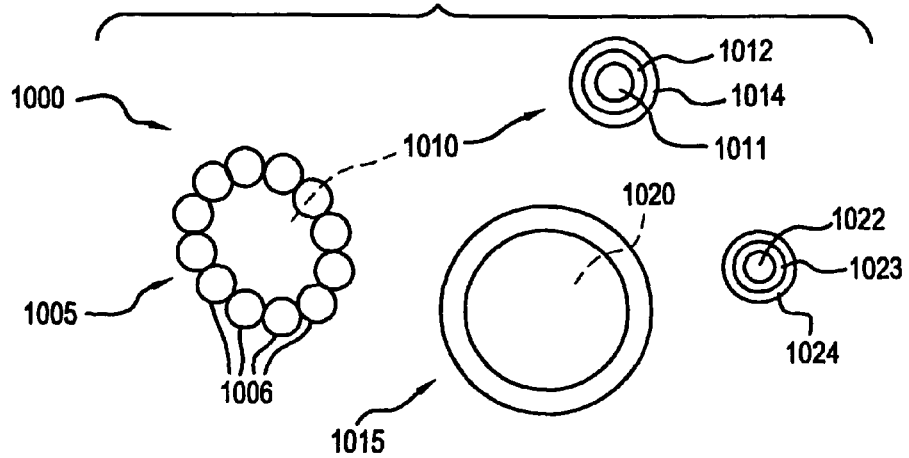
FIG. 23 shows jewelry with photoelastic properties.

FIG. 23 shows jewelry 1000 with photoelastic properties. Jewelry includes bangles, necklaces, bracelets, pens, earrings, rings, body piercing objects, etc. A bracelet or necklace 1005 is made of a series of spherical or other shaped objects 1006. Note that objects 1006 may have embedded magnets to hold the objects together or be held together by string/wire or other device. A cross section 1010 of the objects 1006 shows that each object 1006 is made of a central region 1011 of transparent or translucent photoelastic material surrounded by a polarizing film 1012 and a protective covering 1014. Jewelry 1015 may be formed in a single piece that is flexible or rigid. A cross section 1020 shows that the jewelry 1015 is made of a central region 1022 of transparent or translucent photoelastic material surrounded by a polarizing film 1023 and a protective covering 1024. Light is transmitted by transmission or reflection.

Figure 24:
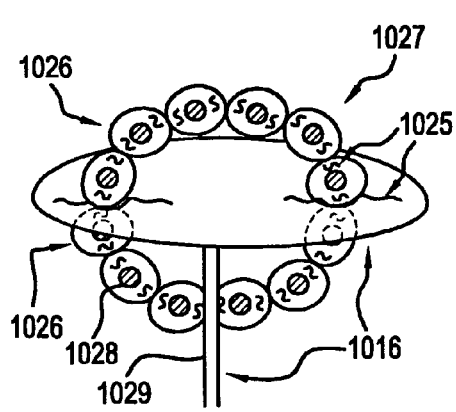
FIG. 24 is a display of spherical photoelastic objects with embedded magnets forming a pattern of circular arches above and below a transparent, translucent, photoplastic and/or photoelastic stand piece.

FIG. 24 is a display 1027 of spherical photoelastic objects 1026 with embedded magnets 1028 forming a pattern of circular arches above and below a transparent, translucent, photoplastic and/or photoelastic stand piece 1016. The arching connected objects 1026 above and below the stand piece 1016 form a construction due to magnetic attractions between objects 1026. The photoelastic effects are due to stress patterns created by the magnetic forces between the objects as well as between the objects and the stand piece. The stand piece 1016 may be circular and may be supported by a vertical rod 1029. Photoelastic and/or photoplastic effects are visible as residual stress patterns as well as stress patterns caused by the interaction of magnetic forces between the objects 1026 and between the objects 1026 and the stand piece 1016.

Figure 25:
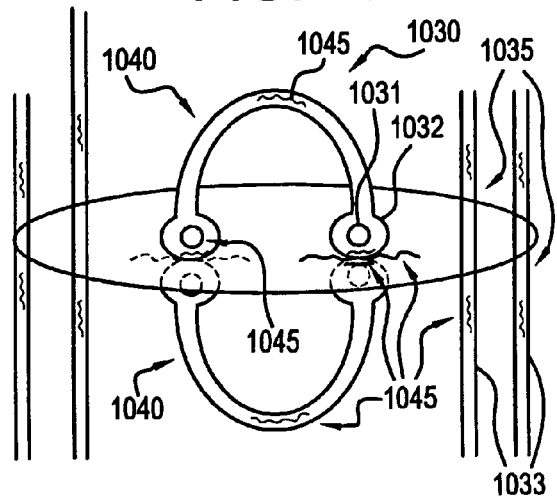
FIG. 25 is a display of dumbbell shaped photoelastic objects with embedded magnets at each spherical shaped end forming an arched pattern above and below another type of transparent, translucent, photoplastic and/or photoelastic stand piece.

FIG. 25 is a display 1030 of dumbbell shaped photoelastic objects 1040 with embedded magnets 1031 at each spherical shaped end 1032 forming an arched pattern above and below another type of transparent, translucent, photoplastic and/or photoelastic stand piece 1035. The arching connected objects 1040 above and below the stand piece 1035 form a construction due to magnetic attractions between objects 1040. Photoelastic effects 1045 are due to stress patterns created by the magnetic forces between the objects as well as between the objects 1040 and the stand piece 1035. The stand piece 1035 may be circular and may be supported by one or more vertical rods 1033. Photoelastic and/or photoplastic effects 1045 are visible as residual stress patterns as well as stress patterns caused by the interaction of magnetic forces between the objects 1040 and between the objects 1040 and the stand piece 1035. The bending of the dumbbell shaped photoelastic objects 1040 causes other stress patterns 1045.

Figure 26:
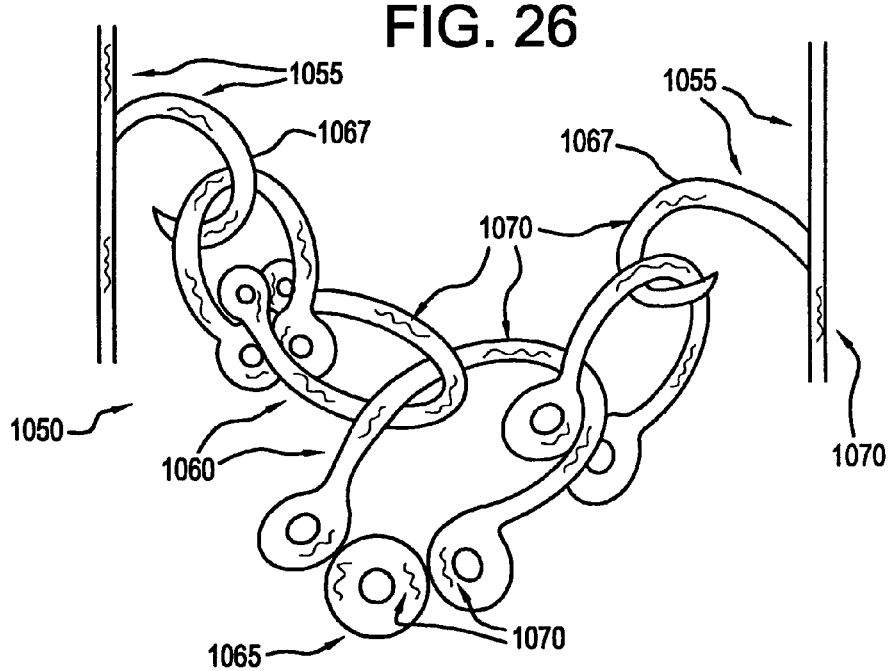
FIG. 26 is a display of dumbbell shaped and one spherical shaped photoelastic objects forming a chain-like pattern suspended by hooked structures from another type of transparent, translucent, photoplastic and/or photoelastic stand piece.

FIG. 26 is a display 1050 of dumbbell shaped 1060 and one spherical shaped 1065 photoelastic objects forming a chain-like pattern suspended by hooked structures 1067 from another type of transparent, translucent, photoplastic and/or photoelastic stand piece 1055. The interlocking chain like pattern forms a construction due to magnetic attractions between the objects. Photoelastic effects 1070 are due to stress patterns created by the magnetic forces between the objects 1060, 1065, by stress caused by bending the cylindrical parts of the dumbbell shaped objects 1060, by gravitational forces from the weight of the hanging chain like construction on the hooked parts 1067 of the stand 1055 as well as on the objects themselves, and by residual stress patterns.

Figure 27:
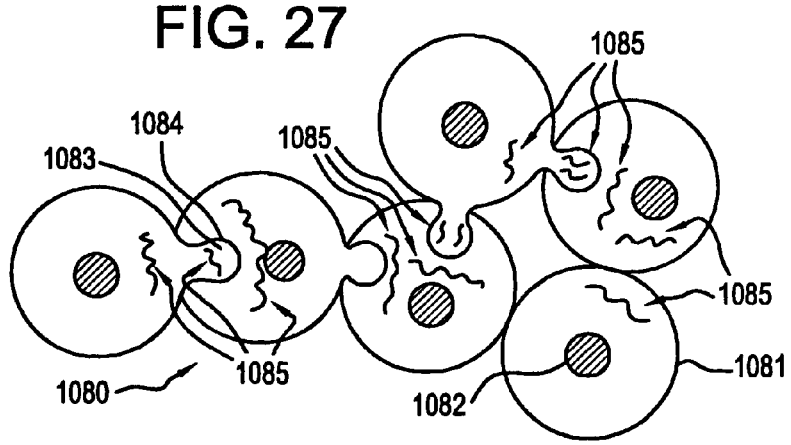
FIG. 27 is an interlocking construction of spherical objects with embedded magnets.

FIG. 27 is an interlocking construction 1080 of spherical objects 1081 with embedded magnets 1082. Some of the spheres 1081 having out pouches 1083, some having in pouches 1084, and some have neither in nor out pouches. Various shapes can be used together. Though not shown here, embedded magnets 1082 may be absent in some of these objects that can connect and create stress patterns from the mechanical forces caused by the interlocking parts alone. Photoelastic stress patterns 1085 are caused in part from mechanical forces of interlocking parts on each other as well as interaction of magnetic forces.

Figure 28:
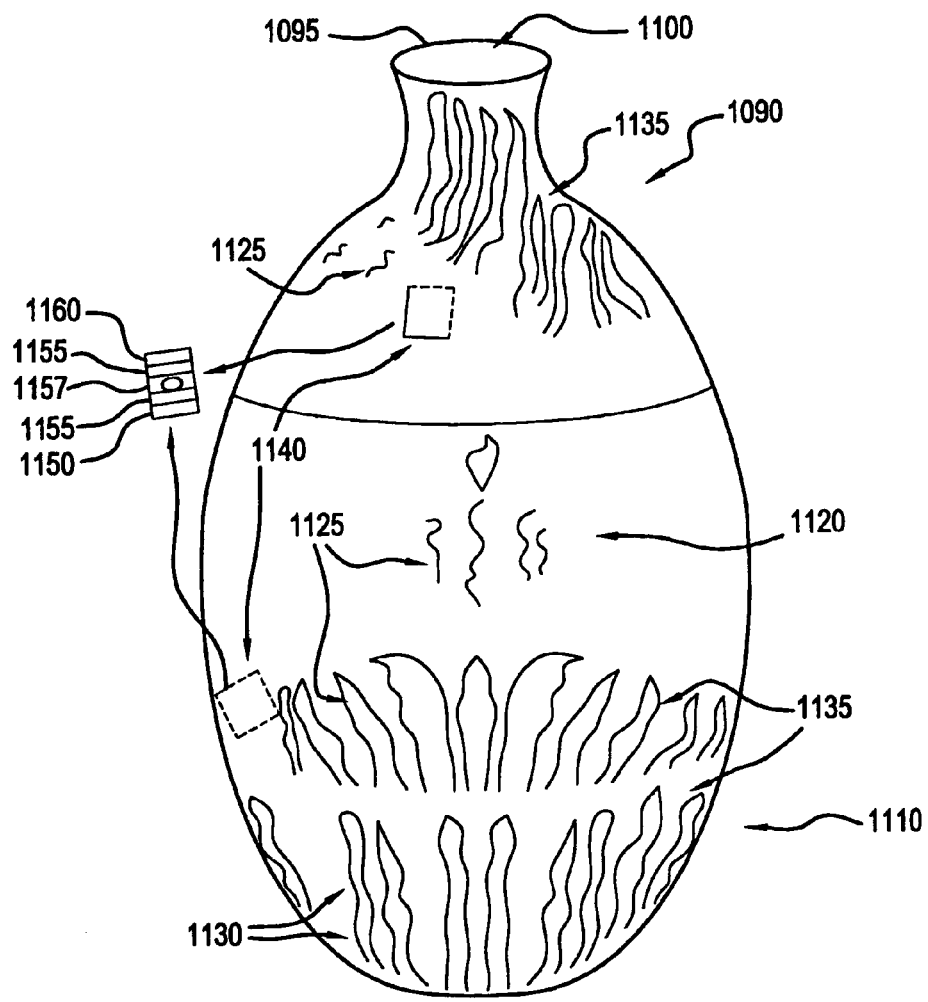
FIG. 28 is a candleholder that displays photoplastic effects due to residual stresses as well as stresses created by active heating and cooling from the light source.

FIG. 28 is a candleholder 1090 that displays photoplastic effects 1125 due to residual stresses as well as stresses created by active heating and cooling from a light source. The photoelastic effects are further exaggerated by opposing materials connected or embedded together that vary in properties such as coefficients of thermal expansion. The light source may also be made of photoelastic/photoplastic/translucent/transparent material that is deformed by a device that compresses it. The burning material 1120 with photoelastic properties is also capable of burning gradually and producing light in a controlled steady manner. This material may be edible or inedible. The burning material 1120 may also be standard candle wax, gel, oil, alcohol, kerosene based material, or similar material that can be opaque, translucent, or transparent in part or in whole.

A lid 1095 of the candleholder 1090 allows for viewing photoelastic patterns 1125 from the holder material by transmission or from photoelastic candle material or from both from above making use of reflection from a mirrored surface 1130 from below. An opening 1100 in the lid 1095 allows gases to escape.

A bottom 1110 of the candleholder 1090 has photoelastic patterns 1125 from the holder material that can be viewed by transmission. Photoelastic stress patterns from photoelastic candle material can be viewed making use of reflection from a mirrored surface 1130 from the bottom and partially on the sides of the candleholder 1090.

Photoelastic stress patterns 1125 created in a photoelastic candle holder 1090 or candle material 1120 can vary as a result of differential heating and cooling. Photoelastic candle material 1120 is preferably made from an oil-based material with thermoplastic resins that forms a gel. A gel with an embedded wick can be molded into any desired shape that can then be placed in a deforming device to create stress patterns. A simple example of such a device is a clear band tied around the gel candle to compress it or two halves of a transparent irregular cup like structure that envelops and compresses the shape of a gel candle when clamped together around the candle. The photoelastic/photoplastic stress patterns in the candle holder and/or candle material may be due to residual stresses within the photoelastic/photoplastic material of the candle holder and/or candle material or caused by deformation from heating and cooling caused by heat from the light source which may be further increased if the photoelastic material is furthered stressed by mechanical forces exerted by differential expansion of combined materials with different thermal properties such as different coefficients of thermal expansion.

The mirrored surface 1130 on the bottom and possibly part of the sides of the candleholder facilitates observation of photoelastic stress patterns 1125 by means of reflection through the candleholder 1090 and candle material 1120 from the mirrored surfaces 1130. Photoelastic material 1135 may be embedded within the candleholder 1090.

Cross sections 1140 of candleholder bottom 1110 and lid 1095 show the layering of materials. Inner surfaces 1150 of candleholder lid and bottom protect the outer layers from excessive heat exposure. Inner layers of polarizing film 1155 facilitate viewing of photoelastic stress patterns within layers of photoelastic embedded materials 1157 by transmission of light. Outer layer of polarizing film 1155 aide viewing of photoelastic stress patterns within layers of photoelastic embedded materials 1157 by transmission as well as the viewing of photoelastic stress patterns of a photoelastic candle and photoelastic embedded materials 1157 by reflection from mirrored surfaces 1130 through the candle material. Finally, a protective outer surface 1160 protects the outer polarizing film 1155 from erosion caused by the elements and handling.

Figure 29:
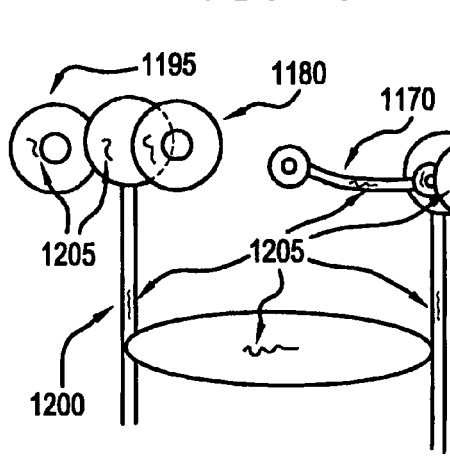
FIG. 29 is a construction using photoelastic objects with embedded magnets on a stand piece that facilitates suspension in space of an object as a result of magnetic forces.

FIG. 29 is a construction 1165 using dumbbell shaped 1170 and spherical shaped 1180, 1190, 1195 photoelastic objects with embedded magnets on a stand piece 1200 that facilitates suspension in space of an object as a result of magnetic forces. A dumbbell shaped photoelastic object 1170, with embedded magnets in spherical shaped ends, is suspended in midair due to a balanced relationship of magnetic attraction between itself and other photoelastic objects with embedded magnets in balanced relationship to gravity and their respective positions on a stand piece 1200.

A spherical photoelastic object 1180 is held firmly against a stand piece 1200 that supports it in an elevated position due to magnetic attraction through the stand piece 1200 to another photoelastic object 1195 with an embedded magnet on the other side of the stand piece 1200. A spherical photoelastic object 1190 with an embedded magnet holds the dumbbell shaped photoelastic object 1170 with embedded magnets in its spherical ends by magnetic attraction through the stand piece 1200 to one end of the dumbbell shaped photoelastic object with an embedded magnet. The suspended end of the dumbbell shaped photoelastic object 1170 is attracted to the objects 1180, 1195 out of reach on the other side of the stand because of the embedded magnets in each of the objects. If the attraction is greater than the gravitational forces, but less than the magnetic forces pulling it in the opposite direction, the free end of the dumbbell shaped object 1170 is suspended. The stand 1200 is a transparent/translucent/photoelastic/photoplastic piece with two vertical disc-like structures with circular planes facing each other, vertical rod like structures supporting the disc-like structures, as well as a horizontal circular platform below.

Photoelastic/photoplastic stress patterns 1205 are caused by residual stress in the stand piece and objects, by forces caused by magnetic interactions, and by bending on the cylindrical part of the dumbbell shaped object suspended in space.

Figure 30:
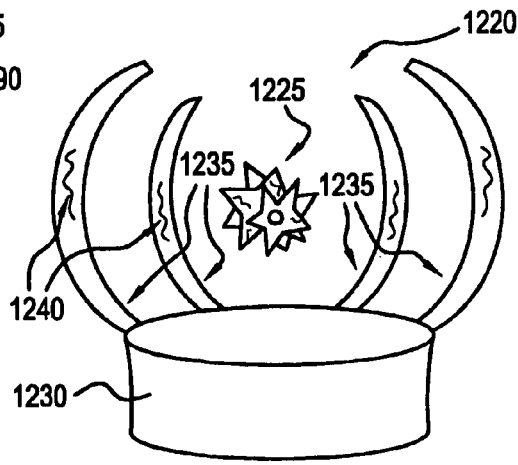
FIG. 30 is a photoelastic object suspended in space.

FIG. 30 is a display 1220 of a photoelastic object 1225 with embedded magnets suspended in space. The photoelastic object 1225 may be spinning or stationary. A variety of levitating devices 1230 are known. In the present case, photoelastic effects 1240 are added to the levitation. In this embodiment, the photoelastic object 1225 or the embedded magnets may have spikes that create residual stress patterns. Other photoelastic displays 1235 compliment the visual effect 1240 of the levitated photoelastic object 1225.

Figure 31:
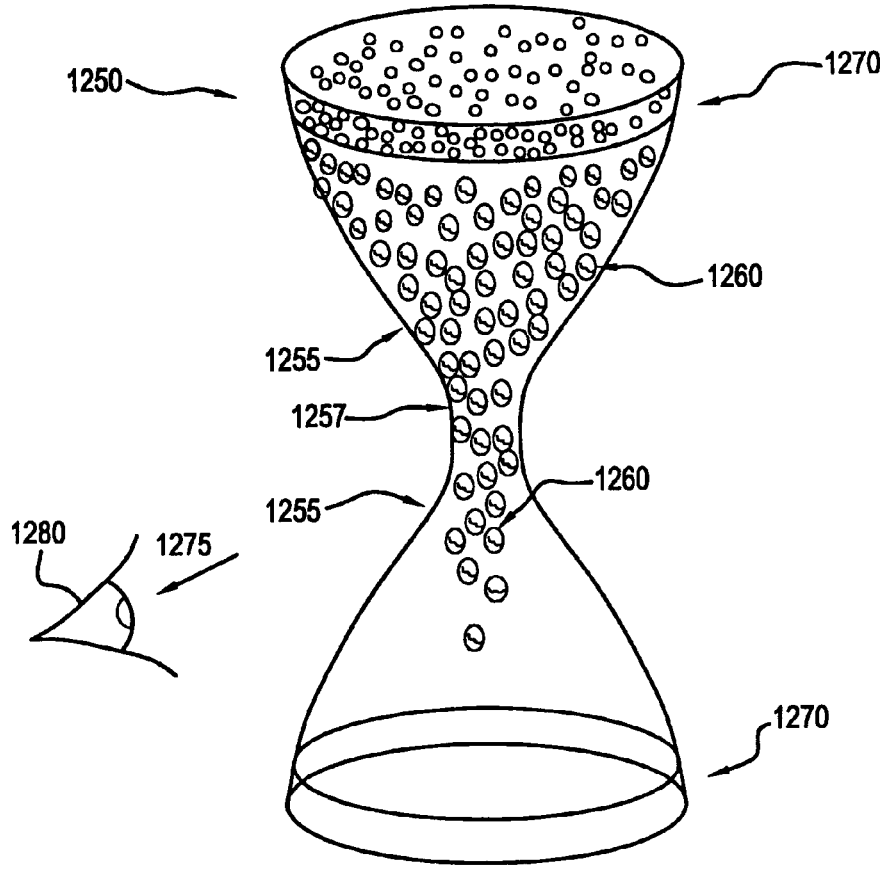
FIG. 31 is an hourglass shaped toy polariscope device.

FIG. 31 is an hourglass shaped toy polariscope device 1250. An hourglass shaped translucent/transparent/photoplastic/photoelastic container 1255 is partly or entirely covered with polarizing film. The container need not be photoplastic/photoelastic if emphasis is on the photoelastic/photoplastic effects of the contents of the container. A narrow segment 1257 various in diameter and constriction shape. The container 1255 also varies in flexibility and can be edible or inedible. Photoelastic/photoplastic/translucent/transparent bead-like structures 1260 are placed within the container 1255. The size and shape of the bead-like structures 1260 are designed in conjunction with the size and shape of the container 1255 and the narrow neck 1257. The bead-like structures 1260 may be edible or inedible and vary in flexibility, hardness, or firmness. The bead like structures or other type of contents need not be photoelastic/photoplastic if emphasis is on the photoplastic/photoelastic effects of the container. The beads 1260 flow through the constriction 1257 like sand through an hourglass and may or may not have timing characteristics. The bead-like structures 1260 may flow through the constriction over and over by turning the hourglass container 1255 over after the bead-like structures 1260 move to the lower half of the container 1255 from the upper half of the container 1255. This may also be accomplished with a motor. A light source may be included. This embodiment of the present invention may further include one or more removable lids 1270 so that contents of the container 1255 are accessible to a user. If the contents of the container 1255 are edible or inedible they can be sold separately as replacements for the container 1255.

Light 1275 from any source, including ambient light, travels through one side of the device, though a polarizing covering on one side of the container 1255, through the photoplastic/photoplastic/translucent/transparent beads 1260 and/or container 1255, through a polarizing covering on the other side of the container 1255, and onto an observer 1280. This embodiment functions due to observation of the photoelastic/photoplastic effects by transmission. If the inner surface of one side of the device 1250 is a mirrored surface, then light 1275 is reflected off the inner surface, passes through the photoelastic/photoplastic/translucent/transparent beads 1260 and/or container 1255, through the other side of the container 1255, through the polarizing covering on the other side of the container, and onto the observer 1280. This embodiment functions due to observation of the photoelastic/photoplastic effects by reflection. This embodiment may be turned or tilted with a motor and involve shapes other than hourglass shapes with any size or shape of beads. It may also involve pouring beads from side to side, spinning the beads around, or having them flow through tube structures or channels within a container of a variety of shapes. This format can enhance other effects such as phosphor or plasma light displays.

The hourglass shaped polariscope device 1250 may also involve any type of passage with flowing beads.

Figure 32:
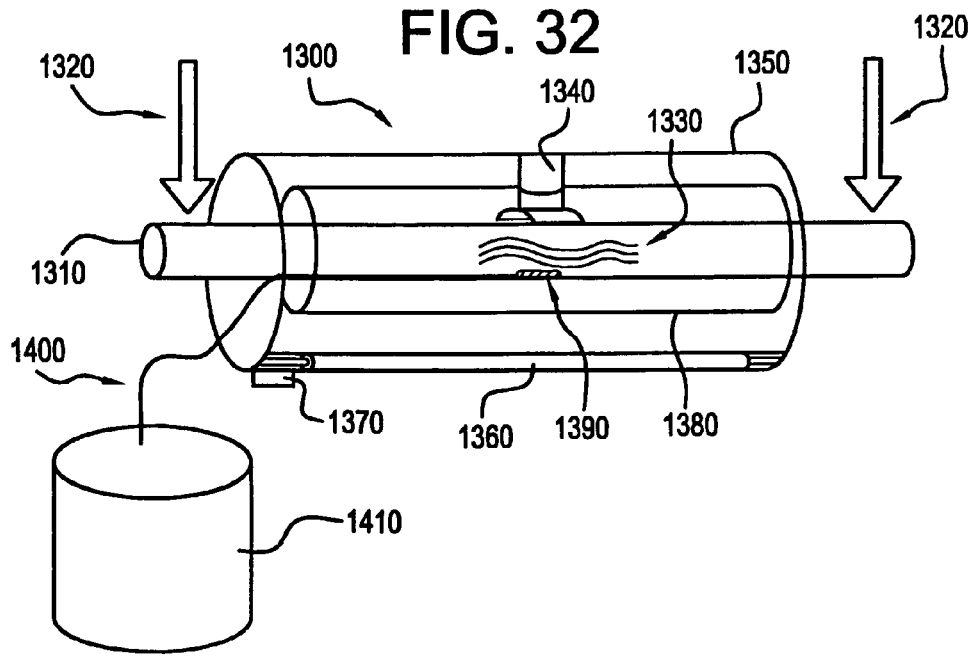
FIG. 32 is a device using photoelastic fringes, visualization of digital output, sound, and animation to stimulate and motivate the user to exert a bending force on a photoelastic rod.

FIG. 32 is a device 1300 using photoelastic fringes, visualization of digital output, sound, and animation to stimulate and motivate the user to exert a bending force on a photoelastic rod. This embodiment not only encourages an interest in science, physics, and engineering, but also motivates the user to do physical exercise. The device 1300 is also applicable to rehabilitation situations and may be modified to work other muscle groups. A bending force 1320 created by a user acts upon a photoelastic rod 1310. The bending force 1320 creates fringes 1330 in the photoelastic rod 1310. A cylinder of polarizing film 1380 surrounds the photoelastic rod 1310 within a chamber housing 1350.

The chamber housing 1350 surrounds the photoelastic rod 1310. A device 1340 within the chamber housing 1350 prevents bending of the photoelastic rod 1310 beyond the strength of the rod 1310. Additional features may include a light illuminating chamber 1360 within the chamber housing 1350 connected to a battery or other power source 1370 for the light 1360. A strain gauge 1390 measures strain on the photoelastic rod 1310. A signal from the strain gauge 1390 is proportional to the force applied 1320. Wires 1400 connect the strain gauge 1390 to an output recorder 1410. The output recorder 1410 converts the signal from the strain gauge 1390 into a usable form. In a preferred embodiment, the output is converted into a visual representation of the force 1320 along with sound and animation.

Figure 33:
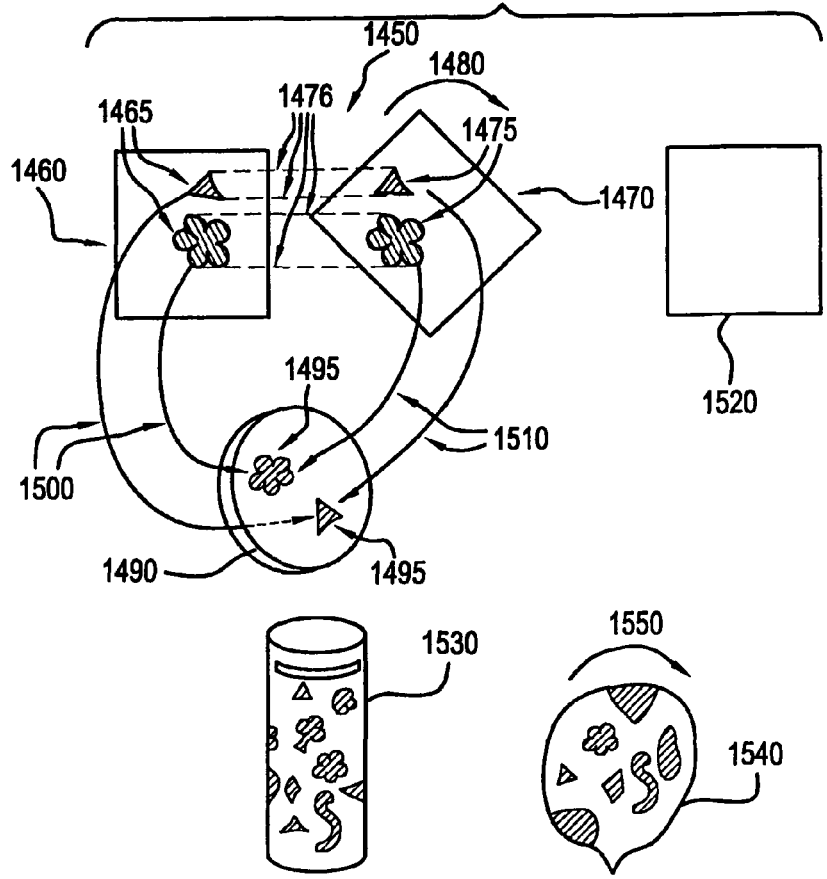
FIG. 33 is a process whereby polarizing films are cut out and graphed onto photoelastic/photoplastic objects in different patterns of orientation to create varying patterns of transmission of light on an object.

FIG. 33 is a process 1450 whereby polarizing films 1460, 1470 are cut out and graphed onto photoelastic/photoplastic objects 1490 in different patterns of orientation to create varying patterns of transmission of light on an object 1490. Cut out portions 1465 of a polarizing film 1460 are created in a variety of patterns. A second polarizing film 1470 is oriented at an angle with respect to the first polarizing film 1460 to specify the amount of light that is transmitted between the two polarizing films 1460, 1470. After an angle of orientation 1480 has been fixed, portions are cut out 1475 of the second polarizing film 1470 in patterns congruent to the cut out portions 1465 in the first polarizing film 1460. Parallel dashed lines 1476 illustrate congruency between the first polarizing film 1460 cutouts 1465 and the second polarizing film 1470 cutouts 1475.

After the first polarizing film 1460 cutouts 1465 and the second polarizing film 1470 cutouts 1475 have been removed, a different angle 1480 may be fixed and new corresponding shaped cutouts 1465, 1475 may be cut in a variety of patterns from the same films or different films. This creates a patchwork of paired films.

The patchworks of various paired cutout films are placed on photoelastic/photoplastic objects 1490. The paired cut out polarizing films 1465, 1475 are placed on the front and back of the photoelastic/photoplastic object 1490 in congruent alignment with each other in terms of their shapes, but at a different orientation with respect to light when the angle 1480 is not zero, 180 degrees or 360 degrees. The cutouts 1465 are placed 1500 on the back of an object 1490, while the cutouts 1475 are placed 1510 on the front of an object 1490.

Modified films 1520 may also involve filters, mirrored surfaces, half and quarter wave films, lenses, fresnel lenses, and other optical films and devices to enhance effects. The additional optical films and devices may be applied below, on top of, or any where with respect to polarizing films or other optical films. Other films, optical devices, or cut portions of polarizing films may also be arranged randomly on a surface of a photoelastic/photoplastic object 1490 or other cylindrical or rounded shaped photoelastic/photoplastic 1530. The devices 1465, 1475 need not be paired or congruent in terms of shape and still create a pattern of varying transmission of light from varying points of view of the object 1490, 1530. Patchwork devices 1465, 1475 may also be incorporated as a patchwork polarizing film and/or other optical film design for amusing effects in or on a device similar to those shown in FIGS. 1-4, 7-10, 15-32, and 34. Device 1540 containing patchwork devices 1465, 1475 parallels device 5 in FIG. 1 that can rotate 1550 and can operate singly or in pairs.

Figure 34:
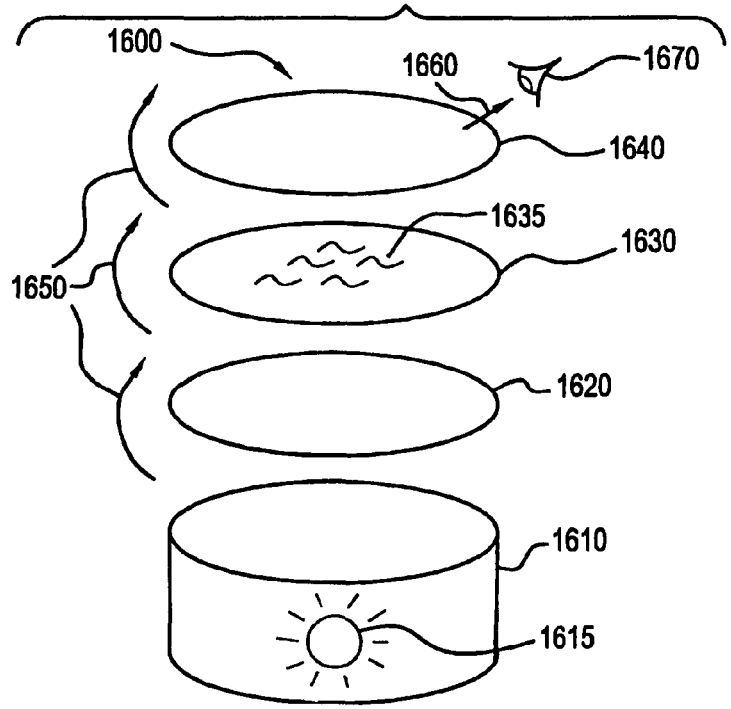
FIG. 34 is an ornamental lamp, light, or light source that may serve as holiday decorations or specialty lights or as a visual stimulus on games or instruments for humans and animals with polarizing films capable of rotation above and below a photoelastic/photoplastic layer fitted above the light source.

FIG. 34 is a lamp, holiday ornamental light, flash light, projecting light, strobe light, visual reward light 1600 on games or instruments for humans and animals, or other light source using a layer of photoplastic\photoelastic material with a display pattern with polarizing films capable of rotation above and below the photoelastic/photoplastic layer fitted above a light source.

A light source 1615 is located in chamber 1610. The light source 1615 may be a steady or flickering light source. The inner surface of the chamber 1610 may also be mirrored to allow for observation by reflection. A polarizing film 1620 is located directly above the light chamber 1610, but below a layer of photoelastic/photoplastic material 1630. Other optical films may likewise be placed here to enhance effects. The layer of photoelastic/photoplastic material 1630 may involve mixed substances that interact with different thermal coefficients of expansion. Different rates of expansion between adjoining, attached substances create stress and stress pattern fringes 1635 on the combination of materials due to effects of heating and cooling from the light source 1615. Fixed stress patterns may also be the result of heating and cooling during the original curing process of the photoelastic/photoplastic material 1630.

Another polarizing film 1640 is located above the layer of photoelastic/photoplastic material 1630. Other optical films may likewise be placed here to enhance effects. The polarizing films 1620, 1640 and the photoelastic/photoplastic material 1630 are capable of rotation 1650 with respect to one another. This controls the transmission of light and the photoelastic/photoplastic display.

Light 1660 travels from the light source in 1615, through the first polarizing film 1620, through the photoplastic/photoelastic layer 1630, through the second polarizing film 1640, and to an observer 1670. This is observation by transmission. To observe by reflection the light from the light source in 1615 is reflected off an inner surface of the chamber 1610, travels through the photoelastic/photoplastic layer 1630, through the polarizing film 1640 above the photoelastic material 1630, and to the observer 1670. Other optical films and devices may be applied anywhere in, on, or around the device to enhance the effect described.

Figure 35:
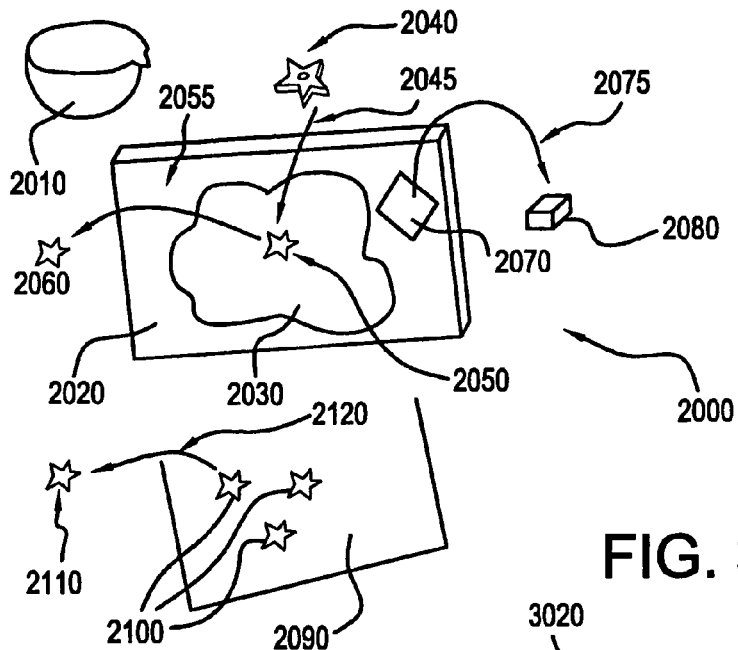
FIG. 35 is an illustration of mixing kits for edible and inedible photoelastic objects.

FIG. 35 is an illustration of mixing kits 2000 for edible and inedible photoelastic objects 2060. A container 2010 has a spout for pouring, mixing, oven heating or microwaving materials while making photoelastic objects 2060. Prepared contents from the container 2010 are poured onto a nonstick surface 2020 for curing into a large object 2030. The nonstick surface 2020 may be modified to allow for controlled heating and measured even thickness. Instead of being in direct contact with the prepared contents, sheets of Teflon or cellophane may serve as an intervening surface to allow cured or partially cured contents to be lifted up and cast onto another object.

A cookie cutter like device 2040 or other similar device may be used to cut out shapes from the large object 2030. The cookie cutter like device 2040 may be a variety of shapes and sizes. The cookie cutter like device 2040 is placed 2045 on the large object 2030 to cut a desired object 2060 out of the large object 2030. The desired object 2060 is removed 2055 from the large object 2030 and leaves a hole 2050.

The resulting photoelastic object 2060 removed from the hole 2050 may be edible (i.e. gelatin based) or inedible (i.e. plastic based).

Prepared contents 2070 on the nonstick surface 2020 are lifted up 2075 and removed from the nonstick surface 2020 for use in casting. An object 2080 on which the prepared contents 2070 are casted is shown.

Alternatively, prepared contents are poured from the container 2010 into a rigid or flexible mold 2090. The rigid or flexible mold 2090 has shaped depressions 2100. After full or partial curing, molded shapes 2110 are lifted or punched out 2120 of the rigid or flexible mold 2090.

Figure 36:
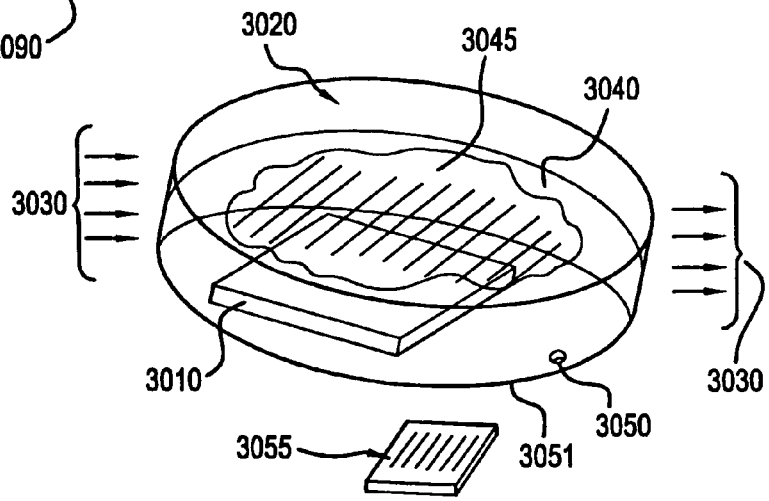
FIG. 36 shows a method of applying an edible or inedible polarizing film on an edible or inedible photoelastic or transparent object.

FIG. 36 shows a method of applying an edible or inedible polarizing film on an edible or inedible photoelastic or transparent object 3010. A container 3020 holds the edible or inedible photoelastic or transparent object 3010 and other contents. Water or oil based fluid 3040 is placed in the container 3020. The water or oil based fluid 3040 may be covered with a fine powder. Layers of molecules 3045 have optical electromagnetic and bifringent properties and spread out forming a thin film on the surface of the water or oil based fluid 3040. The resulting film pushes the fine powder out to the edges on the surface of the liquid making the boundaries of the film visible. An electric current or electromagnetic field 3030 is used to orient the layers of molecules 3045 in a desired direction. A drain 3050 near a base 3051 of the container 3020 is used to remove the water or oil based fluid 3040. As the water or oil based fluid 3040 is drained, the oriented layers of molecules 3045 come to rest on the photoelastic or transparent object 3010.

A resulting coated photoelastic object or transparent object 3055 may in turn be coated on its other sides using a similar process with polarizing orientation at any angle of orientation to the other sides. If the materials involved are edible, an edible photoelastic object may be made, or if applied to the surface of an edible transparent object, the coated edible object may be used as a polarizing device to view objects or even the sky and other environments prior to consumption. If only the polarizing film is edible, it may be licked off inedible surfaces.

Figure 37:
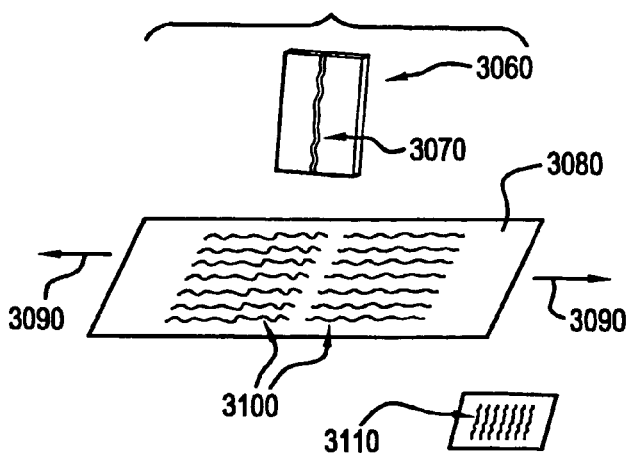
FIG. 37 shows a method of making an edible photoelastic film.

FIG. 37 shows a method of making an edible polarizing film 3110. The process is started with an edible polymer material 3060. The edible polymer material is preferably, but not limited to, starch and protein based materials. Edible chiral molecules 3070 have optical bifringent electromagnetic properties. The edible chiral molecules 3070 may involve doped gold and/or silver or other similar materials, e.g. potassium chloride or sorbate, iodine, dicalcium, sodium bicarbonate or benzoate, carotinoids, alcohols, glycine, glycerine, lecithin, lipids, phospholipids, hydrocarbons, amino acids, certain vitamins, etc.

The edible polymer material 3060 is stretched into a stretched out position 3080. Arrows 3090 show the direction of stretching of the edible polymer material 3060. The edible chiral molecules 3070 are aligned in one orderly direction 3100 determined by the alignment polymers 3060 brought about by stretching to create the stretched out position 3080. The result is the edible polarizing film 3110 that can be used to view objects, the sky, and other environments prior to consumption.

Figure 38:
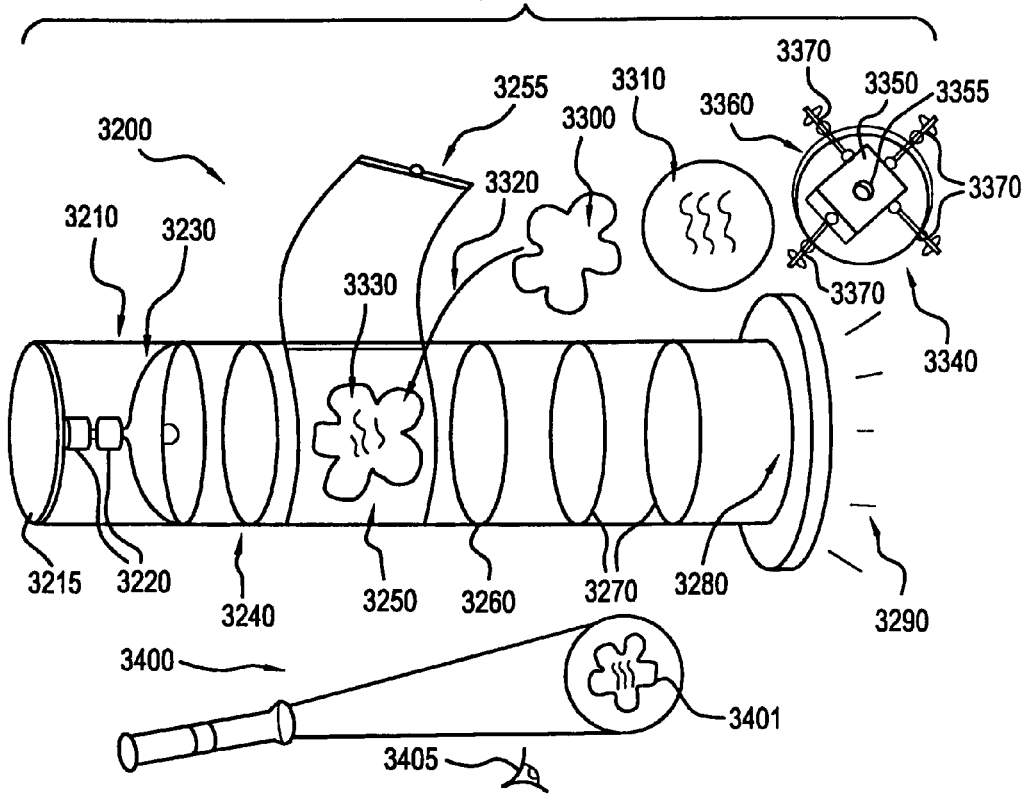
FIG. 38 is an example of a flash light form of a projecting polarizing device.

FIG. 38 is an example of a flash light form 3200 of a projecting polarizing device. A tube 3210 holds contents of the device 3200. The tube 3210 is opened and closed at an end cap 3215 or other device to insert batteries 3220 and other objects. A projecting light source 3230 is located in the tube 3210. A first polarizing film 3240 may rotate in front of the projecting light source 3230 but behind a compartment 3250 for placement of objects to be manipulated and viewed. A second polarizing film 3260 may be located in front of the first polarizing film 3240 and the compartment 3250 and may rotate. A projecting lens array 3270 allows focusing. A portal 3280 allows projected light and its created image to pass out of the tube 3210 in the form of projected light rays 3290.

Photoelastic or other objects 3330 are placed 3320 and manipulated in the compartment 3250. Slide like photoplastic sheets 3310 with fixed fringes may also be placed in the compartment 3250. A hinged door or other opening 3255 allows access to the compartment 3250.

Alternative photoelastic devices 3340 within the device 3200 allows for mechanical manipulation and fixation. A photoelastic object 3350 within device 3200 may have deformities or holes 3355 to enhance photo-stress fringes. A ring or other shaped mounting device 3360 holds the photoelastic objects 3350 and screws and other manipulating devices 3370. The screws and other devices 3370 mechanically stress the photoelastic object 3350. Otherwise photoelastic devices may be manipulated manually or through some other means.

The device 3200 may be formed as a hand held flash light 3400 projecting an image 3401 on a screen or wall for an observer 3405 to see.

Figure 39:
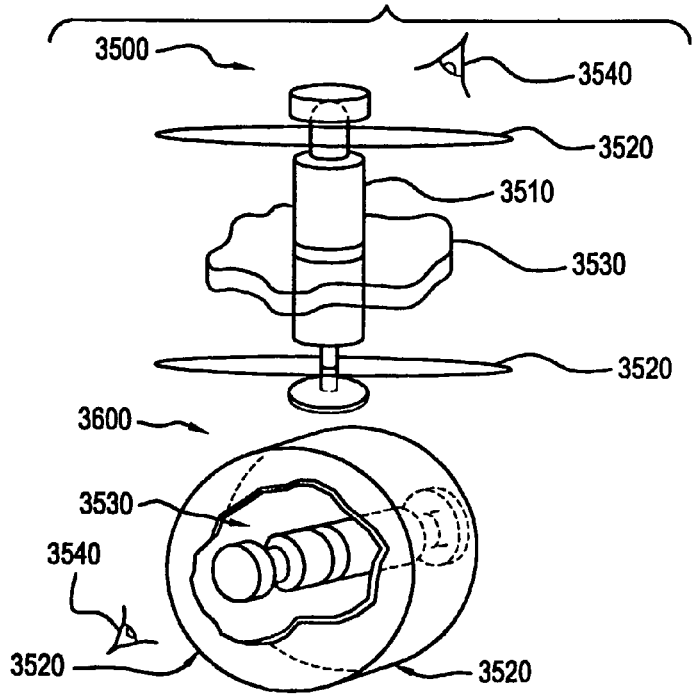
FIG. 39 is a transverse view of a photo elastic object mounted between rotating polarizing films in a device.

FIG. 39 is a transverse view of a photo elastic object 3530 mounted between rotating polarizing films 3520 in a device 3500. The device 3500 may be partly or completely edible. The rotating polarizing films 3520 are mounted like wheels on an axle type device 3510. The photoelastic object 3530 is mounted on the axle 3510 between the rotating polarizing films 3520. The photoelastic object 3530 is manipulated either manually or mechanically and observed at one end of the device 3500 by an observer 3540. The axle device 3500 is also shown from an oblique angle 3600.

Figure 40:
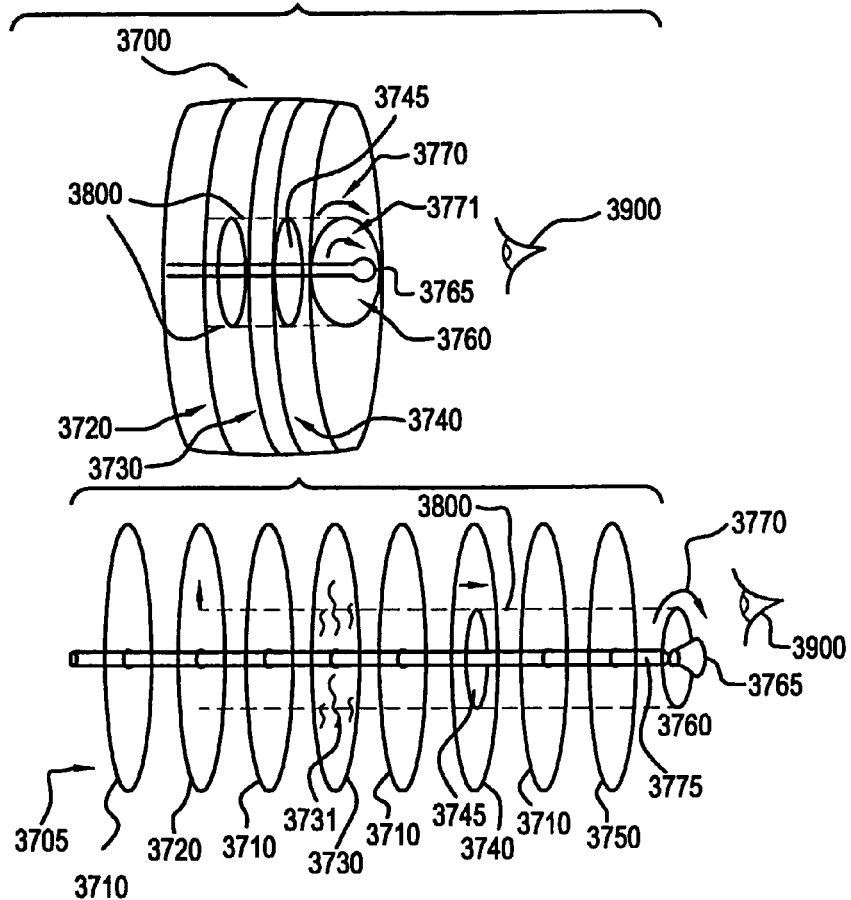
FIG. 40 is a sun catcher type device for viewing a plastic sheet with patterns of fixed fringes impressed within it.

FIG. 40 is a sun catcher type device 3700 for viewing a plastic sheet 3730 with patterns of fixed fringes 3731 impressed within it. The patterns 3731 are designed by imprinted forms or impressing plastic sheets with metallic or other heat tolerant substrates formed into patterns to make the embossed designs. This is a compact view of the device. The device 3700 may be mounted on a light source, or provided with a stand or mounting device to be exposed to sunlight or use ambient light before observance by an observer 3900. An expanded view 3705 of the sun catcher like device 3700 shows details of the layers.

Protective transparent plastic coverings 3710 protect and mount polarizing films 3720, 3740 and the embossed plastic sheet 3730 with fixed photoelastic patterns 3731. The polarizing film 3720 is oriented in a fixed position behind the embossed plastic sheet 3730 with fixed photoelastic patterns 3731. A polarizing film 3740 in front of the embossed plastic sheet 3730 is oriented 90 degrees in a fixed position with respect to the polarizing film 3720.

Additional devices 3750 such as Fresnel lenses, filters, wave plates etc. may be included.

A smaller polarizing film 3760 rotates with respect to a corresponding portion on 3720 through an exposed cut out portion 3745 of the polarizing film 3740.

A knob 3765 allows turning 3771 of the smaller polarizing film 3760 and rotation 3770 of an axel type configuration 3775.

Figure 41:
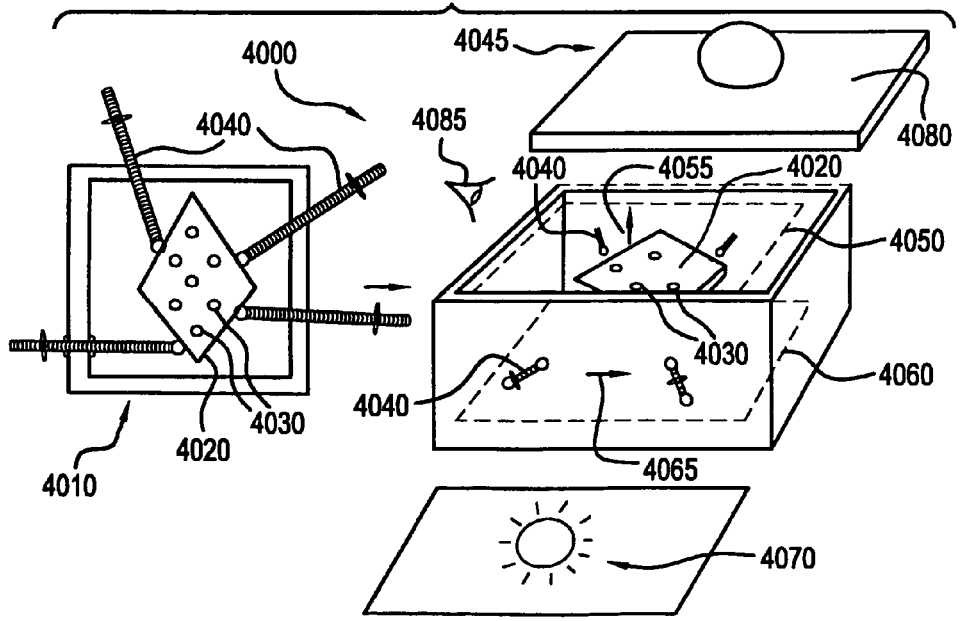
FIG. 41 is a boxed photoelastic device with manipulating screws.

FIG. 41 is a boxed photoelastic device 4000 with manipulating screws 4040. The boxed photoelastic device 4000 has sides of a box 4010. A photoelastic device 4020 is located inside the box 4010. The photoelastic device 4020 may have holes or deformations 4030 to enhance photoelastic stress patterns. The screws 4040 that screw into the box press against the photoelastic device 4020, deforming the photoelastic device 4020 and creating stress patterns.

An oblique and transverse view 4045 of the boxed photoelastic device 4000 shows a first polarizing film 4050 above the photoelastic device 4020 and oriented at 90 degrees with respect to an opposite polarizing film 4060. The first polarizing film 4050 is oriented 4055 at 90 degrees with respect to the orientation 4065 of the opposite polarizing film 4060. The opposite polarizing film 4060 is located below the photoelastic object 4020, but above a light source 4070. A lid 4080 closes the box 4010 from view of an observer 4085.

Figure 42:
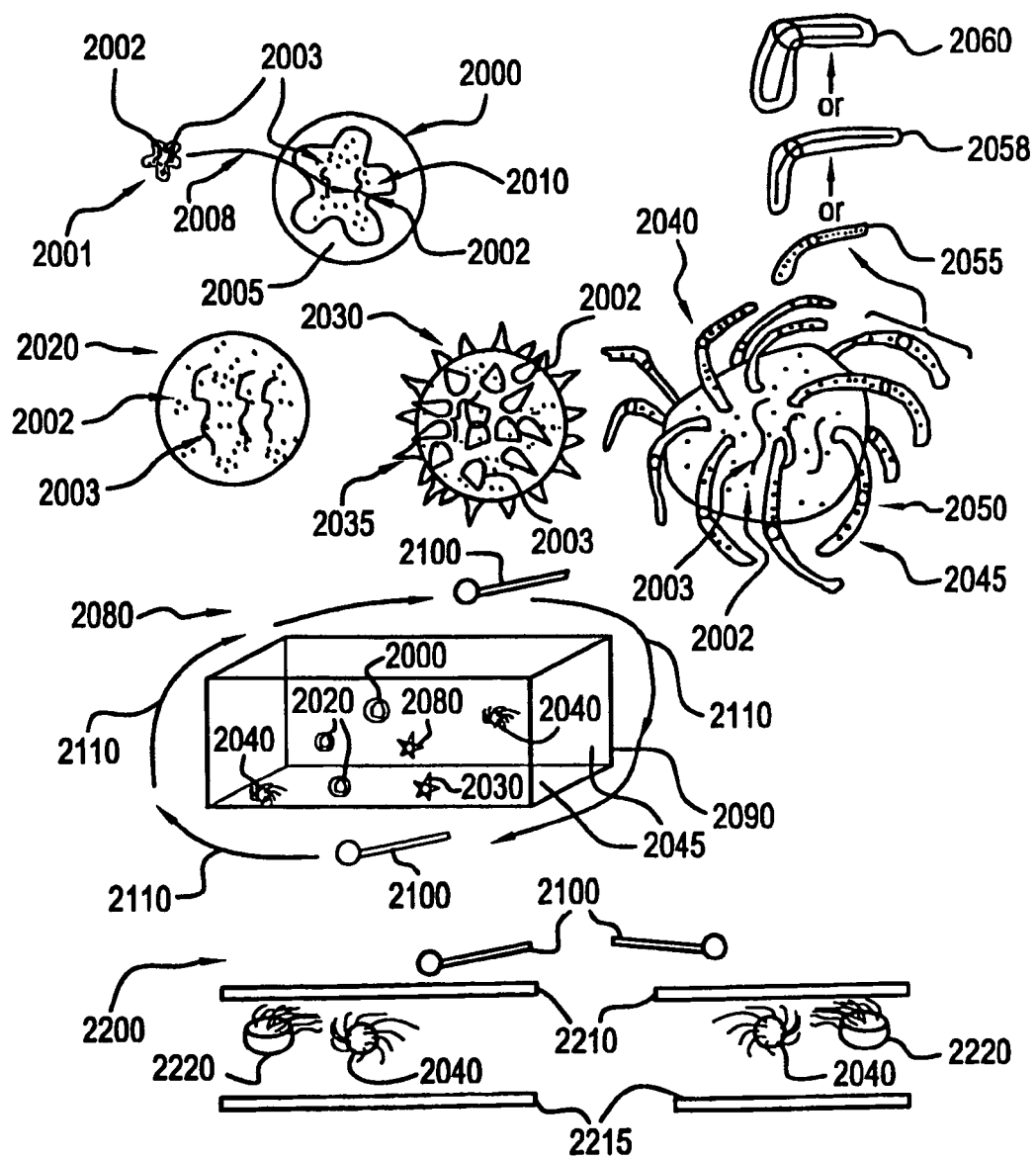
FIG. 42 shows various photoelastic objects with ferromagnetic material incorporated into the photoelastic objects in the form of dust filings, fibers, wires, or larger tubes or sheets with mirrored surfaces.

FIG. 42 shows various photoelastic objects 2000 with ferromagnetic material incorporated into the photoelastic objects in the form of dust filings, fibers, wires, or larger tubes or sheets with mirrored surfaces. The larger tubes may be straight, bent or hinged. Other photoelastic objects with large forms of ferromagnetic material of any shape may also be used. An example of ferromagnetic material is preferably, but not limited to, iron.

Smaller photoelastic objects 2001 have fixed photoelastic fringes 2002 and with ferromagnetic material 2003 incorporated within the smaller photoelastic objects 2001. An image is amplified 2010 when the smaller photoelastic objects 2001 are embedded 2008 inside a translucent/transparent spherical ball 2005. The ferromagnetic material 2003 is preferably, but not limited to, ferromagnetic dust or filings.

Other embodiments 2020 include a photoelastic object 2001, in this example spherical, with ferromagnetic dust or filings 2003 incorporated within the photoelastic object. The object can be of any shape and the ferromagnetic material can be of any size and configuration and shape in other embodiments.

Other embodiments 2030 may include spikes 2035 for creating fringes 2002.

Other embodiments 2040 may include long projections 2045 that may be flexible strands or more rigid, bent or hinged strands or projections. Projections 2055 with hinges 2050 and ferromagnetic dust or filings, or projections 2058 with incorporated fibers or wires, or projections 2060 with larger tubes or sheets with mirrored surfaces may be part of the projections 2045. The projections 2045 may come in a variety of shapes including spiral or spring-like shapes. The projections 2045 may have fixed fringes 2002 as well as produce more fringes on deformation.

Other alternative embodiments of the present invention 2080 use a magnetic wand 2100 to cause movement of photoelastic objects, such as 2000, 2020, 2030 or 2040, with incorporated ferromagnetic material 2002, and/or mirrored surfaces of a variety of configurations within a transparent/translucent box or container 2090 for holding photoelastic objects covered with polarizing film and/or partially covered with mirrored areas 2095. Sides of the container 2090 are covered with polarizing films only or mirrored surfaces with opposing sides with polarizing films or other combinations 2095 to allow for viewing of photoelastic objects by transmission and/or reflection. The magnetic wand 2100 that attracts the photoelastic objects that contain ferromagnetic material causes them to move 2110.

An alternative view 2200 of the container 2090 focuses on objects with projections that move 2040 or remain more stationary 2220. A transparent/translucent barrier 2210 with a polarizing film covers the top of the container 2090 and a transparent/translucent-barrier 2215 with polarizing film or mirror covers the bottom of the container 2090. The photoelastic objects that are more stationary 2220 have projections that move in response to the magnetic field caused by the magnetic wand 2100 because ferromagnetic materials have been incorporated into the objects 2220.

While the invention has been described with reference to specific embodiments, modifications and variations of the invention may be constructed without departing from the scope of the invention.

The invention claimed is:

1. A method for creating photoelastic objects comprising:
   pouring a photoelastic mixture onto a surface,
   forming a desired end shape for entertainment and play for a photoelastic object,
   curing the photoelastic mixture, and
   removing the cured mixture from the surface,
   wherein the photoelastic mixture is edible.

2. The method of claim 1, further comprising adding additives to the photoelastic mixture before curing.

3. The method of claim 1, wherein the forming a desired end shape for entertainment and play for a photoelastic object is performed by bringing two or more semi-polymerized photoelastic pieces of photoelastic mixture together, forming a final composite shape.

4. The method of claim 3, further comprising adding additives to the semi-polymerized photoelastic pieces before the bringing together.

5. The method of claim 1, wherein the forming a desired end shape for entertainment and play for a photoelastic object is performed by curing the photoelastic mixture in a mold with a lid in which there exist one or more projections for forming one or more impressions in the photoelastic object.

6. A method for creating photoelastic objects comprising:
   pouring a photoelastic mixture onto a nonstick surface,
   forming a desired end shape for entertainment and play for a photoelastic object,
   curing the photoelastic mixture, and
   removing the cured mixture from the surface,
   wherein a layer of the photoelastic mixture or an optical polymer is stretched into an edible polarizing film.

7. The method of claim 6, wherein the photoelastic mixture or an optical film is plasticized sugar, starch, gelatin or other polymer with a non-toxic chiral dye with light absorbing and/or non-toxic optically active chemicals like gold, silver, iodine, and/or certain lipids, phospholipids, lecithin, alcohols, caroteniods, vitamins, hydrocarbons, iodine, potassium, calcium, amino acids, glycerine, glycine, and combinations thereof.

8. The method of claim 5, further comprising placing one or more additives in a shape formed in the photoelastic object by the lid.

9. The method of claim 1, wherein the forming a desired end shape for entertainment and play for a photoelastic object is performed by attaching two or more pieces of photoelastic mixture by interlocking them.

10. The method of claim 1, wherein the forming a desired end shape for entertainment and play for a photoelastic object is performed by cutting the photoelastic mixture after it has been cured using a cookie cutter like device.

11. The method of claim 1, wherein the surface is a nonstick mold.

12. The method of claim 1, wherein the desired end shape for entertainment and play is modular for connecting and disconnecting in various configurations.

13. The method of claim 1, wherein the desired end shape for entertainment and play is a creature.

14. The method of claim 1, wherein the forming a desired end shape for entertainment and play for a photoelastic object is performed by curing the photoelastic mixture in a cylindrical mold and slicing the cured photoelastic mixture perpendicular to its central axis.

* * * * *